United States Patent [19]

O'Dorisio et al.

[11] Patent Number: 5,590,656
[45] Date of Patent: Jan. 7, 1997

[54] APPLICATION OF PEPTIDE/CELL RECEPTOR KINETICS UTILIZING RADIOLABELED SOMATOSTATIN CONGENERS IN THE IN SITU, IN VIVO DETECTION AND DIFFERENTIATION OF NEOPLASTIC TISSUE

[75] Inventors: Thomas M. O'Dorisio; M. Sue O'Dorisio, both of Worthington; Edward W. Martin, Jr., Delaware, all of Ohio; Eugene A. Woltering, Kenner, La.

[73] Assignee: The Ohio State University Research Foundation, Columbus, Ohio

[21] Appl. No.: 114,675

[22] Filed: Aug. 31, 1993

Related U.S. Application Data

[63] Continuation-in-part of Ser. No. 945,110, Sep. 15, 1992, abandoned.

[51] Int. Cl.$^6$ .......................................................... A61B 6/00
[52] U.S. Cl. .......................... 128/654; 128/659; 128/898
[58] Field of Search ...................................... 424/1.1, 1.69; 128/653.1, 653.4, 654, 659, 898; 600/1, 3, 4

[56] References Cited

U.S. PATENT DOCUMENTS

| | | | |
|---|---|---|---|
| 4,782,840 | 11/1988 | Martin, Jr. et al. | 128/654 |
| 4,932,412 | 6/1990 | Goldenberg | 120/654 |
| 5,094,837 | 3/1992 | Bis | 128/654 |
| 5,225,180 | 7/1993 | Dean et al. | 424/1.1 |

OTHER PUBLICATIONS

Merck Index, 10th Edition, p. 1246 (1983).
Bakker et al. "Receptor Scintography with Radio–Iodinated Somatustatin Analog" *Journal of Nuclear Medicine*, vol. 31, #9 (Sep. 1990).
Lamberts et al. "Somatostatin Receptor Imaging" *Journal of Steroid Biochem & Molecular Biology*, vol. #37, #6 pp. 1079–1082 (1990).
Lamberts et al. "The Role of Somatostatin" *Endocrine Reviews*, vol. 12, #4, (1991).

(List continued on next page.)

*Primary Examiner*—C. Fred Rosenbaum
*Assistant Examiner*—Chalin Smith
*Attorney, Agent, or Firm*—Mueller and Smith, LPA

[57] ABSTRACT

Broadly, the present invention is directed to a method for the detection and differentiation of neoplastic tissue in a patient suspected of having neoplastic tissue. The method includes the administration of a radiolabeled somatostatin congener to the patient and accessing the patient with a radiation detection probe for determining tissue exhibiting elevated levels of radiation, viz., neoplastic tissue. However, before subjecting the patient to such administration, an initial determination preferably is made as to whether the radiolabeled somatostatin congener will bind to the tumor site, i.e., whether somatostatin receptors are associated with the neoplastic tissue. This is conveniently done with a wide variety of endocrine tumors, which release peptides or hormones, referred to as "biochemical markers." In order to make this determination, initially a biochemical marker-inhibiting dose of unlabeled somatostatin congener is administered to the patient. The biochemical marker associated with the neoplastic tissue then is monitored to determine whether the administered somatostatin congener reduces the presence of the marker in the patient. If the monitored presence of the marker was reduced, then the surgeon can be confident that the neoplastic tissue or tumor contains receptors to which the somatostatin will bind. Thus, the administration of radiolabeled somatostatin congener is appropriate for such patient. If the biochemical marker associated with the neoplastic tissue is not appropriately reduced following the administration of the unlabeled somatostatin congener, then the neoplastic tissue may not be determinable by the use of radiolabeled somatostatin congener and alternative modalities of treatment should be considered, such as the use of radiolabeled antibodies as proposed in U.S. Pat. No. 4,782, 840. If the tumor is of a type that does not release a biochemical marker, the presence of somatostatin receptors can be confirmed by other means, such as pathology, immunohistochemistry, radioreceptor assay, or such other means as will be apparent to those skilled in the art.

33 Claims, 13 Drawing Sheets

TISSUES 9C v 10C

OTHER PUBLICATIONS

Harris, "Future Medical Prospects for Sandostatin" *Metabolism,* vol. 39, #9, suppl 2 (Sep. 1990) pp. 180–185.

O'Dorisio et al. "Somatostatin and Somatostatin–like Peptides: Clinical Researchand Clinical Applications" *Advances in Endocrinology and Metabolism,* vol. 1, Mosha Year Book, 1990.

O'Dorisio et al., "Somatostatin and Somatostatin–like Peptides: Clinical Research and Clinical Application", Advances in Endocrinology and Metabolism, vol. 1, pp. 175–230, Mazzaferri et al., eds.

O'Dorisio et al., "Rationale for Somatostatin Therapy and its Clinical Application as the Congener, Octreotide Acetate", Endocrine Cancer, Mazzaferri et al., eds.

Harris, "Future Medical Prospects for Sandostatin, Metabolism", vol. 39, No. 9, Suppl. 2 (Sep.) 1990: pp. 180–185.

Lamberts et al., "Treatment with Sandostatin and In Vivo Localization of Tumors with Radiolabeled Somatostatin Analogs", Id at pp. 152–155.

Bakker et al., "Receptor Scintigraphy with a Radioiodinated Somatostatin Analog: Radiolabeling, Purification, Biologic Activity, and In Vivo Application in Animals", J. Nucl. Med, 1990, 31: 1501–1509.

Lamberts et al., "Somatostatin Receptor Imagin In Vivo Locatization of Tumors with a Radiolabeled Somatostatin Analog", J. Steroid Biochem, Molec. Biol., vol. 37, No. 6, pp. 1079–1082 (1990).

Reubi, et al., "In Vitro and In Vivo Detection of Somatostating receptors in Phenochromocytomas and Paragangliomas", J. Clin. Endocrinol. Metab., vol. 74, pp. 1082–1089 (1992).

Krenning et al., "Somatostatin Receptor Imaging of Endocrine Gastrointestinal Tumors", Schwiez med. Wschr., 1992, 122: 634–637.

Reubi et al., "Somatostatin Receptor Incidence and Distribution in Breast Cancer Using Receptor Autoradiography: Relationship to EGF Receptors", Int. J. Cancer, 46, 416–420 (1990).

Pantev et al., "Evaluation of Somatostatin Receptors in Human Cancer", Wien Klin Wochenschr, (1991) 103/21, 649–653.

Lemaire et al., "Disposition of Sandostatin, A New Synthetic Somatostatin Analogue, in Rats", Drug Metabolism and Dispotion, vol. 17, No. 6, pp. 699–703 (1989).

Kwekkeboom et al., "Radiodinated Somatostatin Analog Scintigraphy in Small–Cell Lung Cancer", J. Nucl. Med. 1991, 32: 1845–1848.

Krenning, et al., "Somatostatin Receptor Scintigraphy with Indium–111 DTPA–D–phe–1Octreotide in Man: Metabolism, Dosimetry and Comparison with iodine–123–Tyr–3–Octreotide", J. Nucl. Med. 1992, 33: 652–658.

Lamberts et al., "The Role of Somatostatin and Its Analogs in the Diagnosis and Treatment of Tumors", Endocrine Reviews, vol. 12, No. 4, pp. 450–482 (1991).

Battershill et al., "Octreotide: A Review of its Pharmacodynamic and Pharmacokinetic Properties, and Therapeutic Potential in Conditions Associated with Excess Peptide Secretion" Drugs, 38 (5), 658–702 (1989).

Katz, et al. "Octreotide, A New Somatostatin Analogue", Clinical Pharmacy, vol. 8, Apr. 1989, pp. 255–273.

Lamberts, "A Guide to the Clinical Use of the Somatostatin Analogue SMS 201–995 (Sandostatin)", Acta Endocrinolgica (Copenh), 1987, Suppl. 286, pp. 54–66.

Evers et al., "Somatostatin and Analogues in the Treatment of Cancer", Annals of Surgery, Mar. 91 213(3), pp. 190–198.

Foekens et al., "Prognostic Value of Receptors for Insulin––like Growth Factor 1", Somatostatin and Epidermal Growth Factor in Human Breast Cancer, Cancer Res., 1989; 49:7002–7005.

Moody et al., "Regulation of the Release of Bombesin–like Peptides from Lung Tumors", Regul. Peptides, 1987; 19: 128–132.

O'Dorisio, et al., "Role of Peptide Radioimmunoassay in Understanding Peptide–Peptide Interactions and Clinical Expression of Gastroenteropancreatic Endocrine Tumors", The American Journal of Medicine, vol. 82 (suppl. 5B), pp. 60–67 (1987).

Reichlin, "Editorial" Clinical Application of Somatostatin Receptor Imaging, Journal of Clinical Endocrinology and Metabolism, vol. 71, No. 3, pp. 564–565 (1990).

Patel, "Somatostatin–Receptor Imaging for the Detection of Tumors", The New England Journal of Medicine, vol. 323, No. 18, pp. 1274–1276 (1990).

Krenning, et al., "Localisation for Endocrine–Related Turmors with Radioiodinated Analogue of Somatostatin", The Lancet, pp. 242–244, Feb. 4, 1989.

Schally, "Oncological Application of Somatostatin Analogues" Cancer Research 48, 6977–6985, Dec. 15, 1988.

Lamberts, et al., "Parallet in Vivo and in Vitro Detection of Functional Somatostatin Receptors in Human Endocrine Pancreatic Tumors: Consequences with Regard to Diagnosis, Localization, and Therapy", Journal of Elinical Endocrinology and Metabolism, vol. 71, No. 3, pp. 566–574.

Malarkey, et al., "Responses of GH–and TSH–Secreting Pituitary Adenoma to a Somatostatin Analogue (SMS 201–995): Evidence that GH and TSH Coexist in the Same Cell and Secretroy Granules", Neuroendocrinology 1989; 49: 267–274.

Kvols, et al., "Treatment of the Malignant Carcinoid Syndrome, Evaluation of Long–Acting Somatostatin Analogue", The New England Journal of Medicine, vol. 315, No. 11, pp. 663–666 (1986).

Lee, et al., "Effects of Epidermal Growth Factor and Analogues of Luteinizing Hormone–Releasing Hormone and Somatostatin on Physphorylation and Dephosphorylation of Tyrosine Residues of Specific Protein Substates in Various Tumors", Proc. Natl. Acad. Sci, USA, vol. 88, pp. 1656–1660 (1991).

Beck-Peccoz, et al., "Treatment of Inappropriate Secretion of Thyrotropin with Somatostatin Analog SMS 201–995", Hormone Res. 29: 121–123 (1988).

Lamberts, "Somatostatin Analogs in the Management of Gastrointestinal Tumors", Hormone Res. 29: 118–129 (1988).

Hearn, et al., "Lung Carcinoid with Cushing's Syndrome": Control of Serum ACTH and Cortisol Levels Using SMS 201–995 (Sandostatin), Clinical Endocrinology 28, pp. 181–185 (1988).

Yamada, et al., "Clining and Functional Charactrization of a Family of Human and Mouse Somatostatin Receptors Expressed in Brain", Gastrointestinal Tract, and Kidney, Proc. Natl. Acad. Sci USA, vol. 89 pp. 251–255 (1992).

Tran, et al., "Two Types of Somatostain Receptors Differentiated by Cyclic Somatostatin Analogs", Science, vol. 228, pp. 492–495 (Apr. 26, 1985).

Cuttitta, et al., "Bombesin–Like Paptides Can Function as Autocrine Growth Factors in Human Small–Cell Lung Cancer", Nature, vol. 316:29, pp. 823–826 (1985).

Comi, et al., "Response of Thyrotropin–Secreting Pituitary Adenomas to a Long–Acting Somatostatin Analogue", The New England Journal of Medicine, vol. 317, No. 1, pp. 12–17 (1987).

Maton, et al., "Use of Long–Acting Somatostating Analog SMS 201–995 in Patients with Pancreatic Islet Cell Tumors", Digestive Diseases and Sciences, vol. 34, No. 3, pp. 28S–39S, (Suppl. Mar., 1989).

Vinik, et al., "Use of Somatostatin Analog in Management of Carcinoid Syndrome", Digestive Diseases and Sciences, vol. 34, No. 3, pp. 14S–27S, (Suppl. Mar., 1989).

Klign, et al., "Growth Factor–Receptor Pathway Interfering Treatment by Somatostatin Analogs and Suramin: Preclinical and Clinical Studies", J. Steroid Biochem, Molec. Biol., vol. 2, No. 6, pp. 1089–1095 (1990).

Guillausseau, et al., "Visual Improvement with SMS 201–995 in a Patient with a Thyrotropin–Secreting Pituitary Adenoma", The New England Journal of Medicine, vol. 317, No. 1, pp. 53–54 (1987).

Manni, et al., "Somatostatin Analogues in the Treatment of Breast and Prostrate Cancer", J. Steroid Biochem. Molec. Biol., vol. 37, No. 6, pp. 1083–1087 (1990).

Reubi, et al., "Somatostatin Receptors in Malignant Tissues", J. Steroid Biochem. Milec. Biol., vol. 37, No. 6, pp. 1073–1077 (1990).

Jerkins, et al., "Medullary Carcinoma of the Thyroid, Pancreatic Nesidioblastosis and Microadenosis, and Pancreatic Polypeptide Hydersecretion: A New Association and Clinical and Hormonal Responses to Long–Acting Somatostatin Analog SMS 201–995", Journal of Clinical Endocrinology.

Reubi, et al., "Hormone–Producing Gastrointestinal Tumors Contain a High Density of Somatostatin Receptors", Journal of Clinical Endocrinology and Metabolism, vol. 65, No. 6, pp. 1127–1134 (1987).

Reubi, et al., "High Incidence of Somatostatin Receptors in Human Meningiomas: Biochemical Characterization", Journal of Clinical Endocrinology and Metabolism, vol. 63, No. 2, pp. 433–438 (1986).

Reubi, et al., "High Density of Somatostatin Receptors in Pituitary Tumors from Acromegalic Patients", Journal of Clinical Endocrinology and Metabolism, vol. 59, pp. 1148–1151 (1984).

Lamberts, et al., "Successful Treatment with SMS 201–995 of Cushing's Syndrome Caused by Ectopic Adrenocorticotropin secretion from a Metastic Gastrin–Secreting Pancreatic Islet Cell Carcinoma", Journal of Clinical Endocrinology and Metabolism, vol. 67, No. 5, pp. 1080–1083.

Wemeau, et al., "Long Term Treatment with the Somatostatin Analog SMS 20–1–995 in a Patient with a Thyrotropin–and Growth Hormone–Secreting Pituitary Adenoma", Journal of Clinical Endocrinology and Metabolism, vol. 66, No. 3, pp. 636–629 (1988).

Koch, et al., "Characterization of the Cyclic AMP–Independent Actions of Somatostatin in GH Cells", The Journal of Biological Chemistry, vol. 263, No. 1, pp. 226–234 (1988).

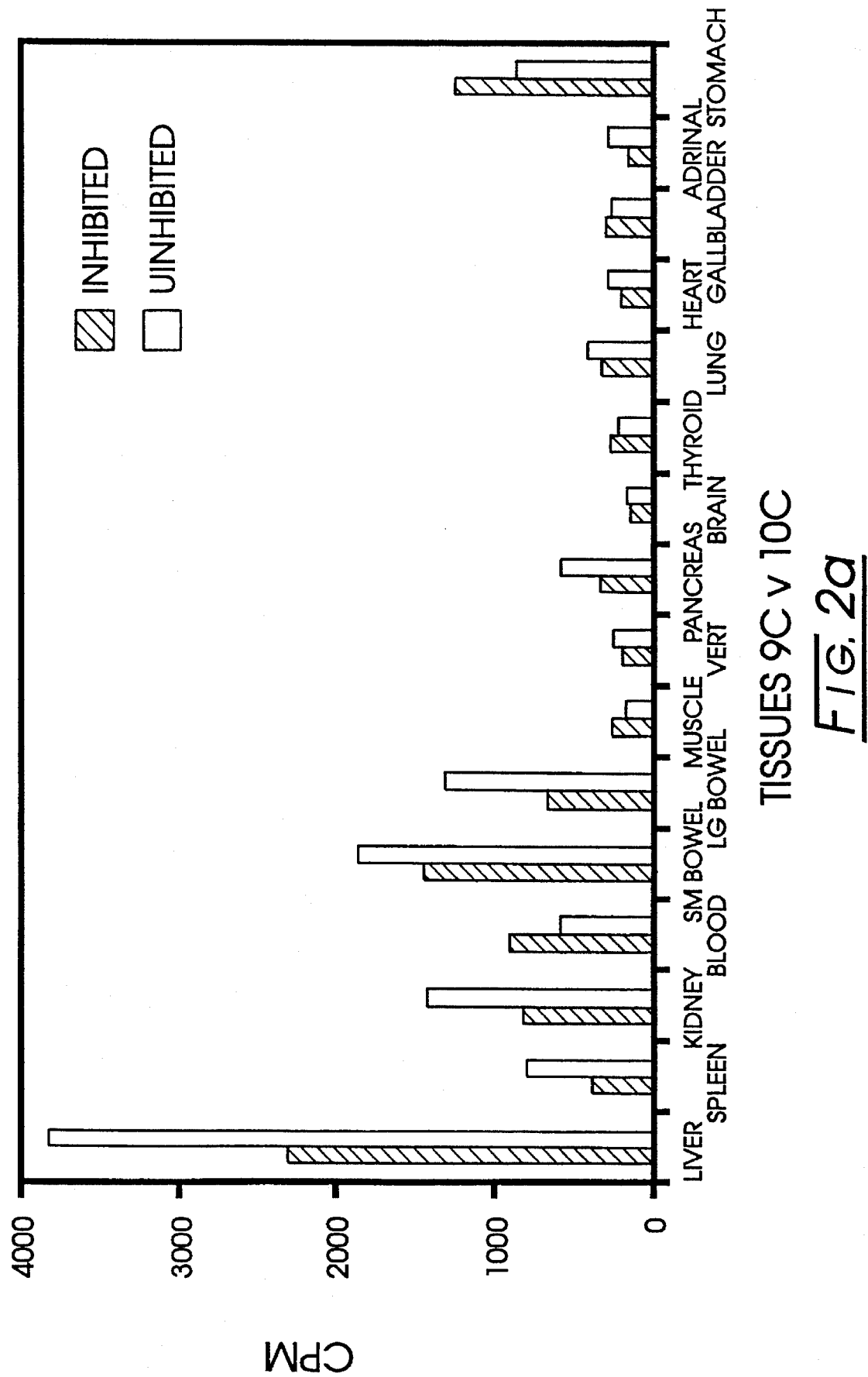

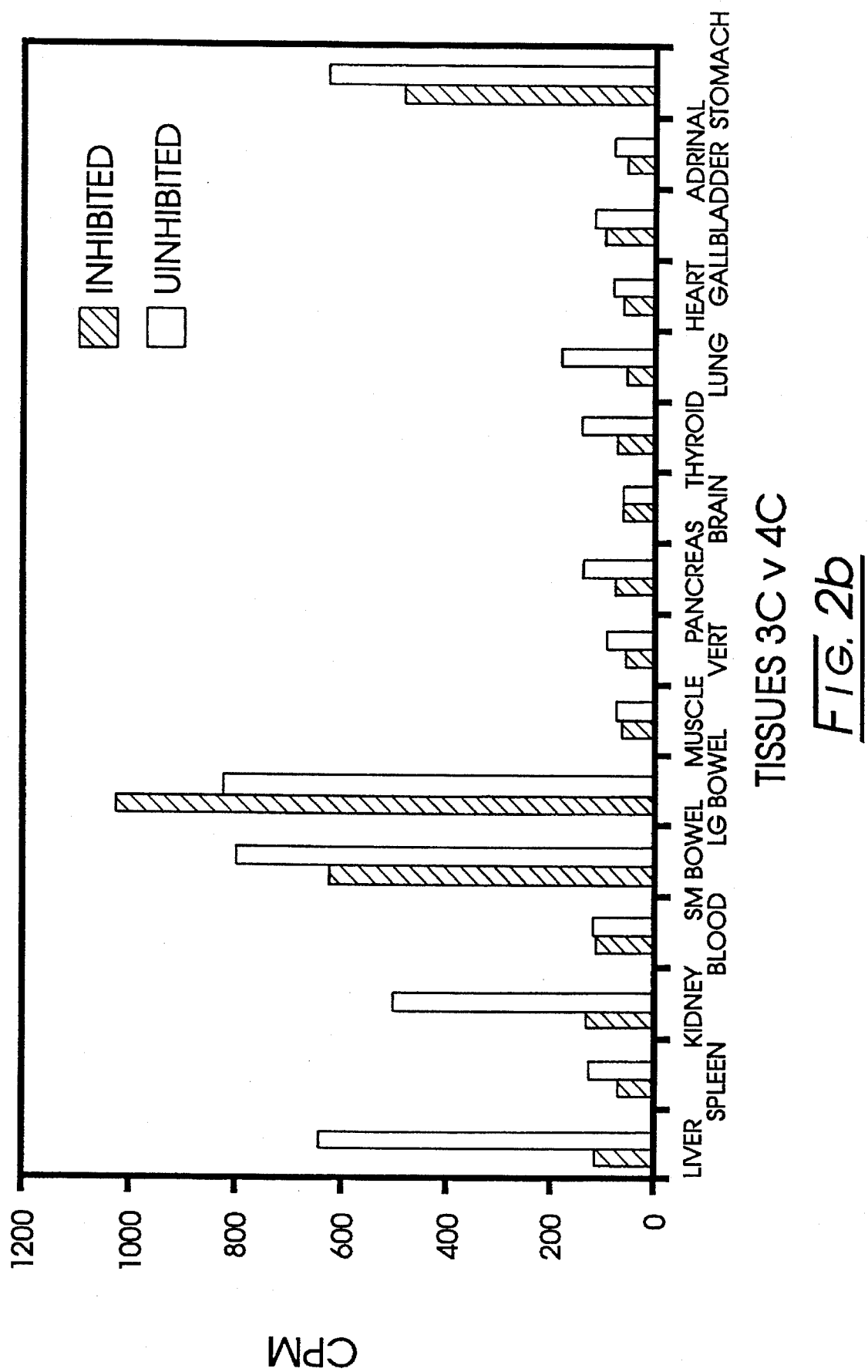

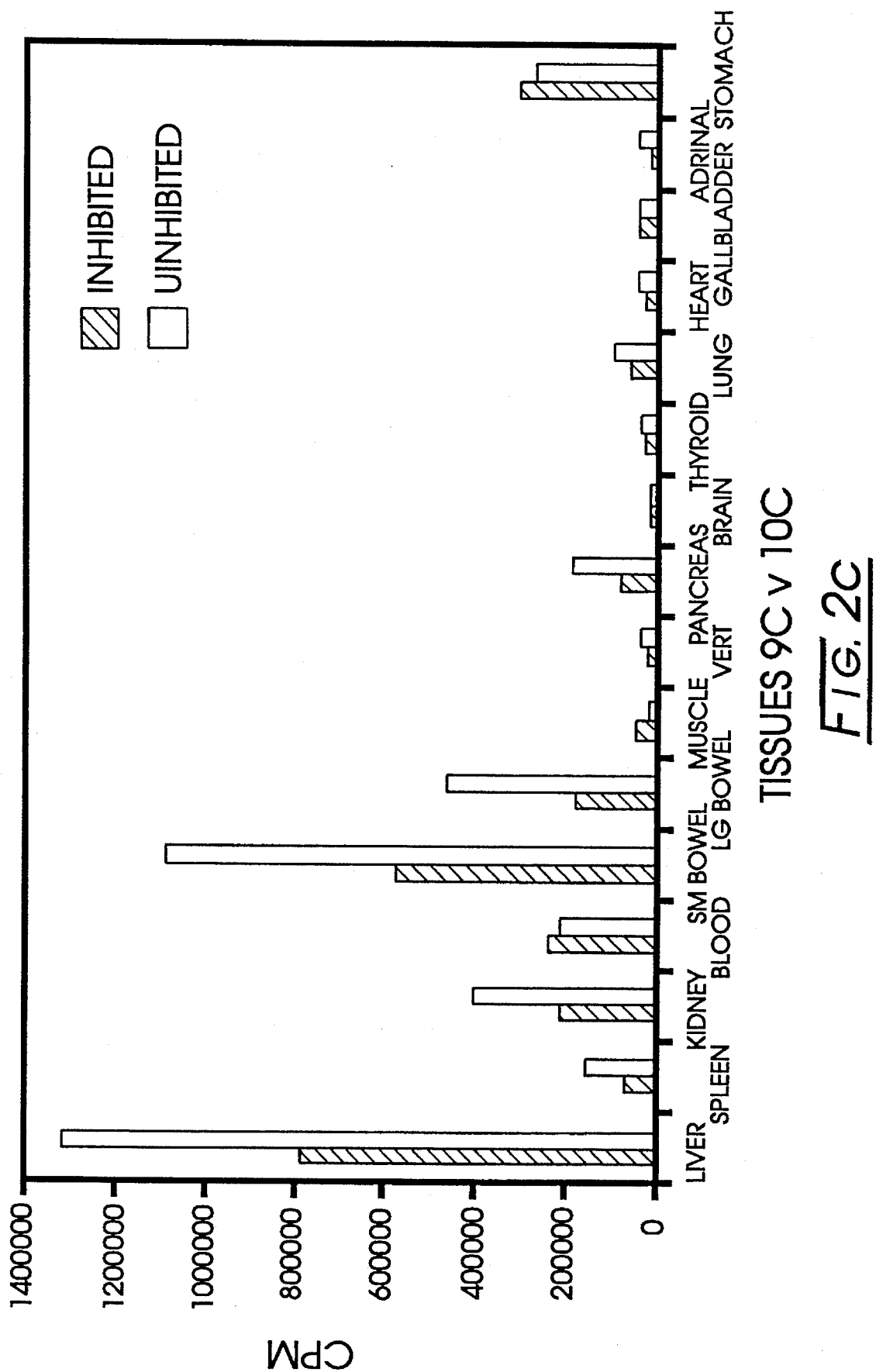

APPLICATION OF PEPTIDE/CELL RECEPTOR KINETICS UTILIZING RADIOLABELED SOMATOSTATIN CONGENERS IN THE IN SITU, IN VIVO DETECTION AND DIFFERENTIATION OF NEOPLASTIC TISSUE

CROSS-REFERENCE TO RELATED APPLICATIONS

This application is a continuation-in-part of application Ser. No. 07/945,110, filed Sep. 15, 1992, now abandoned, the disclosure of which is expressly incorporated herein by reference.

BACKGROUND OF THE INVENTION

The present invention relates to the surgical management of cancer patients and more particularly to a technique for determining, i.e., detecting and differentiating, neoplastic tissue or tumors in cancer patients utilizing somatostatin congeners.

Endogenously produced somatostatin exerts tonic inhibition on release of several pituitary peptides including growth hormone, adrenocorticotropin hormone, prolactin, and thyroid stimulating hormone. Prolactin has mitogenic properties in both endocrine cells and normal lymphocytes; thus, somatostatin or its congeners may exert antiproliferative effects on any endocrine tumor which is stimulated by prolactin, such as breast and prostate cancers. Somatostatin also inhibits release of several intestinal peptides such as insulin, glucagon, motilin, gastric inhibitory peptide (GIP), vasoactive intestinal peptide (VIP), secretin, cholecystokinin, bombesin, and gastrin releasing peptide (GRP). This latter peptide stimulates proliferation of normal and malignant intestinal epithelial cells. GRP also stimulates the proliferation of normal bronchial epithelial cells and is an autocrine growth factor in small cell lung carcinoma.

Two principal molecular forms of somatostatin are known: somatostatin-14 (S-14) and somatostatin-28 (S-28). The structural differences appear to influence the relative degree of inhibitory activity that these molecules exert on the biologic functions which they regulate. S-14 is a 14-amino acid peptide with a cyclic molecular structure stabilized by a disulfide bond between cysteine residues (positions 3 and 14 from the amino-terminal group) and by hydrogen and hydrophobic bond. The amino acid sequence of S-14 is strikingly constant among vertebrate species, including man: (H)-Ala-Gly-Cys-Lys-Asn-Phe-Phe-Trp-Lys-Thr-Phe-Thr-Ser-Cys-(OH). S-28 is a 28-amino acid peptide that contains the same amino acid sequence as S14, but has 14 additional amino acids attached to the amino-terminal end.

Studies of structure-activity relationships among a variety of synthetic somatostatin-like peptides have revealed that the biologic activity of somatostatin resides primarily in four amino acids within the ring structure: $Phe_7$-Trp-Lys-$Thr_{10}$. By eliminating amino acids that are not required for biologic activity and adding non-biologic D-amino acids to reduce enzymatic degradation, chemists have produced a variety of somatostatin-like-peptides that are more potent and longer acting than native somatostatin. For example, octreotide acetate, a synthetic somatostatin analogue, is 45 to 70 times more potent than native somatostatin in inhibiting growth hormone release. Octreotide acetate contains only eight amino acids in the following sequence: D-Phe-Cys-$Phe_3$-D-Trp-Lys-Thr-Cys-Thr-(ol). lanerotide, also a synthetic somatostatin analogue and an octapeptide, is 20 to 50 times more potent than native somatostatin. It is similar to octreotide but bears a D-β-naphthylalanine in the first position and a valine in the sixth position, and has been tyrosinated in the third position.

Somatostatin receptors have been identified in endocrine and non-endocrine human tumors using audioradiographic techniques (e.g., adenomas, meningiomas, mediastinal carcinoid tumors, intestinal carcinoma, and mammary carcinomas). Biochemical characterization of somatostatin binding to cell membranes prepared from human meningiomas and pituitary adenomas has revealed specific, high-affinity somatostatin receptors. Somatostatin receptors in human pituitary adenomas are comparable to somatostatin receptors in normal rat pituitary tissue with respect to their binding characteristics, although human adenomas have higher receptor densities. The presence of somatostatin receptors in tumor tissues may be of clinical interest if such receptors can be linked to the anti-proliferative properties of somatostatin.

Somatostatin and octreotide acetate, the aforementioned synthetic analogue, are ringed structures which do not contain a tyrosine moiety. The addition of tyrosine enables such compounds to be radiolabeled by means of a standard chloramine-T iodination procedure, utilizing, for example, either $^{1231}I$ or $^{1251}I$. Tyrosinated forms of native somatostatin (bearing a tyrosine moiety at either the 1 or 11 position) have been shown to be impractical since they are susceptible to enzyme degradation. However, it has been found that various tyrosinated analogues of somatostatin are resistant to circulating and membrane enzyme degradation and can be exploited for radioiodination use. One such analogue is tyrosinated octreotide acetate. Octreotide acetate (which is referred to variously in the literature as Sandostatin® or SMS 201–995 or simply octreotide) is tyrosinated at the 3 position and thus referred to as $Tyr^3$-octreotide: D-Phe-Cys-$Tyr_3$-D-Trp-Lys-Thr-Cys-Thr-(ol). A second tyrosinated compound which is preferred for use in accordance with the present invention is lanresotide (also known as Somatuline® or BIM 23014), an octapeptide having the following amino acid sequence: D-β-Nal-Cys-$Tyr_3$-D-Trp-Lys-Val-Cys-Thr-($NH_2$).

Further information can be found by reading O'Dorisio et al., "Somatostatin and Somatostatin-like Peptides: Clinical Research and Clinical Applications", *Advances in Endocrinology and Metabolism*, vol. 1, pp. 1.75–230, Mazzaferri et al., eds. (Mosby Year Book, 1990); O'Dorisio et al., "Rationale for Somatostatin Therapy and its Clinical Application as the Congener, Octreotide Acetate", *Endocrine Cancer*, Mazzaferri et al., eds. (to be published); Harris, "Future Medical Prospects for Sandostatin, *Metabolism*, vol. 39, no. 9, suppl. 2 (September) 1990, pp. 180–185; Lamberts et al., "Treatment with Sandostatin and In Vivo Localization of Tumors with Radiolabeled Somatostatin Analogs", Ibid at pp. 152–155; Bakker et al, "Receptor Scintigraphy with a Radioiodinated Somatostatin Analogue: Radiolabeling, Purification, Biologic Activity, and In Vivo Application in Animals", *J. Nucl. Med.*, 1990, 31: 1501–1509; Lamberts et al., "Somatostatin Receptor Imaging In Vivo Localization of Tumors with a Radiolabeled Somatostatin Analog", *J. Steroid Biochem. Molec. Biol.*, vol. 37, no. 6, pp. 1079–1082 (1990); Reubi et al., "In Vitro and in Vivo Detection of Somatostatin Receptors in Pheochromocytomas and Paragangliomas", *J. Clin. Endocrinol. Metab.*, vol. 74, pp. 1082–1089 (1992); Krenning et al., "Somatostatin Receptor Imaging of Endocrine Gastrointestinal Tumors", *Schwiez. med. Wschr.*, 1992, 122: 634–637; Reubi et al., "Somatostatin Receptor Incidence and Distribution in Breast Cancer Using Receptor Autoradiography: Relationship to EGF Receptors", *Int. J. Cancer*, 46, 416–420 (1990); Pantev et at., "Evaluation of Somatostatin Receptors in Human Cancer", Wien Klin Wochenschr, (1991) 103/21: 649–653; Lemaire et al., "Disposition of Sandostatin, a New Synthetic Somatostatin Analogue, in Rats", *Drug Metabolism and Disposition*, vol. 17, no. 6, pp. 699–703 (1989); Kwekkeboom et at., "Radioiodinated Somatostatin Analog Scintigraphy in Small-Cell Lung Cancer", *J. Nucl. Med.*, 1991, 32: 1845–1848; Krenning et at., "Somatostatin Receptor Scintigraphy with Indium-111-DTPA-D-Phe-1-Octreotide in Man: Metabolism, Dosimetry and Comparison with Iodine-123-Tyr-3-Octreotide", *J. Nucl. Med.*, 1992, 33: 652–658; Lamberts et al., "The Role of Somatostatin and Its Analogs in the Diagnosis and Treatment of Tumors", *Endocrine Reviews*, vol. 12, no. 4, pp. 450–482 (1991); B altershill et al., "Octreotide: A Review of its Pharmacodynamic and Pharmacokinetic Properties, and Therapeutic Potential in Conditions Associated with Excess Peptide Secretion", Drugs, 38 (5), 658–702 (1989); Katz et al., "Octreotide, A New Somatostatin Analogue", *Clinical Pharmacy*, vol. 8, Apr. 1989, pp. 255–273; Lamberts, "A Guide to the Clinical Use of the Somatostatin Analogue SMS 201–995 (Sandostatin)", *Acta Endocrinologica* (Copenh), 1987, suppl. 286, pp. 54–66; and Evers et al., "Somatostatin and Analogues in the Treatment of Cancer", *Annals of Surgery*, Mar. 91 213 (3), pp. 190–198, the disclosures of all of the foregoing being expressly incorporated herein by reference.

BROAD STATEMENT OF THE INVENTION

Broadly, the present invention is directed to a method for the detection and differentiation of neoplastic tissue in a patient suspected of having neoplastic tissue. The method includes the administration of a radiolabeled somatostatin congener to the patient and accessing the patient with a radiation detection probe for determining tissue exhibiting elevated levels of radiation, viz., neoplastic tissue. However, before subjecting the patient to such administration, an initial determination preferably is made as to whether the radiolabeled somatostatin congener will bind to the tumor site, i.e., whether somatostatin receptors are associated with the neoplastic tissue. This is conveniently done with a wide variety of endocrine tumors, which release peptides or hormones, referred to as "biochemical markers." In order to make this determination, initially a biochemical marker-inhibiting dose of unlabeled somatostatin congener is administered to the patient. The biochemical marker associated with the neoplastic tissue then is monitored to determine whether the administered somatostatin congener reduces the presence of the marker in the patient. If the monitored presence of the marker was reduced, then the surgeon can be confident that the neoplastic tissue or tumor contains receptors to which the somatostatin will bind. Thus, the administration of radiolabeled somatostatin congener is appropriate for such patient. If the biochemical marker associated with the neoplastic tissue is not appropriately reduced following the administration of the unlabeled somatostatin congener, then the neoplastic tissue may not be determinable by the use of radiolabeled somatostatin congener and alternative modalities of treatment should be considered, such as the use of radiolabeled antibodies as proposed in U.S. Pat. No. 4,782,840, the disclosure of which is expressly incorporated herein by reference. This assumes, of course, that the particular type of neoplastic tissue under consideration is associated with a specific biochemical marker. If the tumor is of a type that does not release a biochemical marker, the presence of somatostatin receptors can be confirmed by other means, such as pathology, immunohistochemistry, radioreceptor assay, or such other means as will be apparent to those skilled in the art. Pre-operative external imaging or scintigraphy also may be used to determine somatostatin congener binding affinity in some cases.

For in vivo, in situ detection with a radiation detecting probe, the preferred radiolabel is $^{125}I$ which is used to label lanreotide or $Tyr^3$-octreotide, the preferred somatostatin congeners. Advantageously, the radiolabeled somatostatin congener is administered to the patient while the patient is in the operating room, as determination of tissue exhibiting elevated levels of radiation can be detected with a radiation detection probe shortly following such administration, for example, as short as one hour or less.

Advantages of the present invention include the ability to conduct an initial screening of cancer patients in order to determine whether the disclosed radiolabeled somatostatin congener will localize neoplastic tissue. Another advantage is the ability to access the patient with the radiation detection probe almost immediately following administration of the labeled somatostatin congener. A further advantage is the ability of the radiolabeled somatostatin congener to be used in the determination of occult tumor in cancer patients. Yet another advantage is the ability of the somatostatin congener to bind with a variety of tumor types, especially including neuroendocrine tumors. These and other advantages will be readily apparent to those skilled in the art based upon the disclosure contained herein.

BRIEF DESCRIPTION OF THE DRAWINGS

As more fully described in the Examples.

DETAILED DESCRIPTION OF THE INVENTION

Figure 1A:
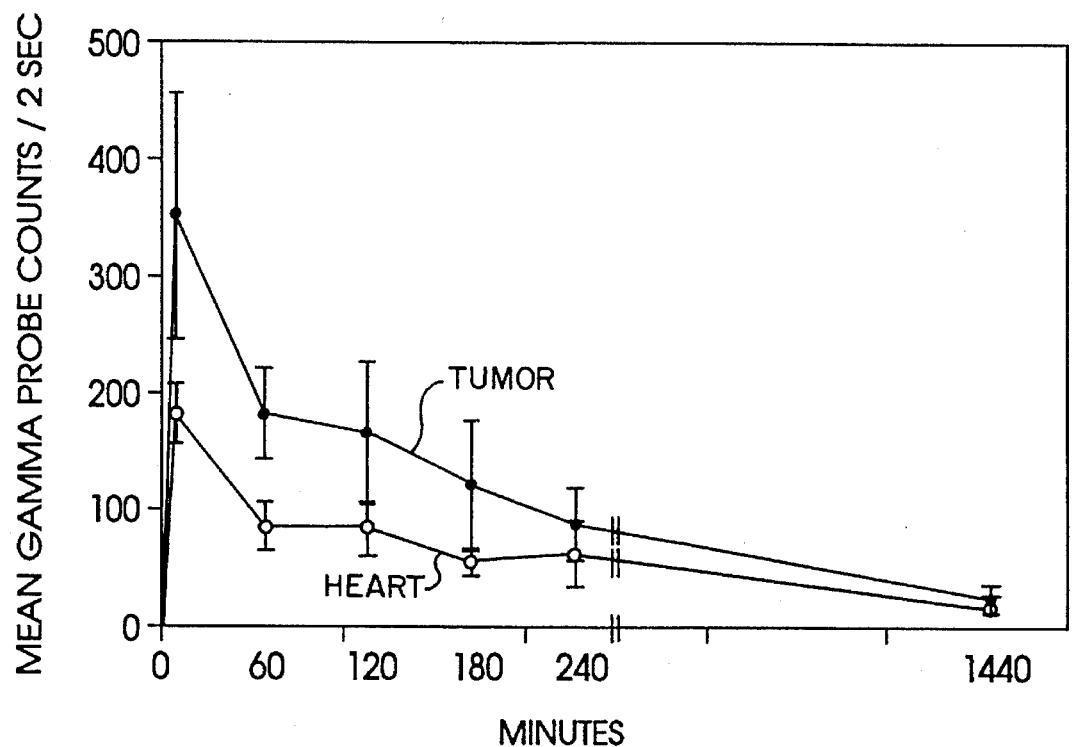
FIG. 1 compares the in vivo binding of $^{125}I$-$Tyr^3$-octreotide in SKNSH versus IMR32 xenografts.

The ability to screen patients in order to ascertain their suitability for treatment in accordance with the present invention resides in the recognition that a variety of tumors contain receptors that bind somatostatin and its congeners, as well as the expression by certain of such tumors of a biochemical marker which is mediated by somatostatin and its congeners. Somatostatin receptors are found throughout the cell, including the cell membrane, Golgi apparatus, endoplasmic reticulum, vesicles, and nucleus. The release of peptides or hormones (i.e., biochemical markers) by certain tumors having somatostatin cell receptors is inhibited by native somatostatin or its synthetic analogues. For example, somatostatin infusions have been shown to suppress the release of a number of pancreatic and gastrointestinal peptides including glucagon, gastrin, gastric inhibitory peptide (GIP), vasoactive intestinal peptide (VIP), pancreatic polypeptide, cholecystokinin (CCK), motilin, and secretin. Because of this diffuse hormonal suppression, the effect of somatostatin and its congeners on functional endocrine tumors can be quantified by measuring hormone, or marker, levels before and after somatostatin administration.

Examples of major endocrine tumors of the gastroenteropancreatic system include gastrinomas which release gastrin, carcinoid tumors which release serotonin, VIPomas which release VIP, glucagonomas which release glucagon, insulinomas which release insulin, GRFomas which release growth hormone releasing factor, PPomas, which release pancreatic polypeptide, medullary thyroid cancer which releases calcitonin, pheochromocytomas which release norepinephrine or epinephrine, and somatostatomas which release somatostatin. Of the aforementioned tumors, gastrinomas appear to be the most common. These tumors are primarily found in the pancreas, although they may also be found in other sites including the stomach, jejunum, omentum, ovary, liver, and parapancreatic lymphatic tissue. Approximately 60% of gastrinomas are malignant, and 50–80% of all patients with malignant gastrinomas have metastases at the time of diagnosis, usually to the liver. The major obstacle to surgical extirpation of these tumors is preoperative localization, which is often not possible using conventional methods such as ultrasound and computerized tomography. In contrast, metastatic lesions as small as 3 mm have been detected using the method of the present invention, thus enabling their removal at an easily resectable stage.

The presence of somatostatin receptors in OAT small cell lung cancer also has been demonstrated. It is believed that the inhibition by somatostatin and its congeners of autocrine growth factors such as gastrin releasing peptides (GRP) may prove important in this type of cancer (Moody et al, "Regulation of the Release of Bombesin-like Peptides from Lung Tumors", *Regul. Peptides*, 1987; 19: 128–132; and references cited above). As the body of knowledge increases with respect to the presence of somatostatin receptors in additional neoplastic tissue or tumors with associated hormone or peptide release, additional types of cancer may find the inventive method efficacious therefor also.

While endocrine tumors are the most prevalent tumors with somatostatin cell receptors, such receptors have also been implicated in connection with other types of cancer. It is believed that somatostatin's influence with respect to non-endocrine tumors may still be hormonally mediated. For example, the presence of somatostatin receptors in breast cancer has been reported (Foekens et al., "Prognostic Value of Receptors for Insulin-like Growth Factor 1, Somatostatin and Epidermal Growth Factor in Human Breast Cancer," *Cancer Res.*, 1989; 49: 7002–7005; and references cited above), which means that monitoring IGF-1 and GH, as well as insulin, may prove important in the determination of breast cancer using radiolabeled somatostatin and its congeners. In tissue culture of human breast cancer lines, somatostatin and octreotide inhibited growth in a dose-dependent manner (Seytano-Han et al., "Direct Inhibitory Effects of Somatostatin (Analogs) on the Growth of Human Breast Cancer Cells," *Cancer Res.*, 1987; 47: 156–1570), up to 40% in one study (Scambia et al., Antiproliferative Effects of Somatostatin and the Somatostatin Analog SMS 201–995 on Three Human Breast Cancer Cell Lines," *J. Cancer Res. Clin. Oncol.*, 1988; 114: 306–308).

Nervous system tumors such as neuroblastomas and medulloblastomas also express somatostatin receptors (O'Dorisio et al., "Characterization of Somatostatin Receptors on Human Neuroblastoma Tumors," *Cell Growth and Differentiation*, in press). With such tumors there is often no recognized biochemical marker susceptible to preoperative suppression by the administration of a somatostatin congener, so it may be necessary to confirm the presence of suspected somatostatin receptors by some other method, as discussed supra.

Since the patient will in most instances receive somatostatin congener administration twice, it may be important to limit the initial dose of unlabeled somatostatin congener to a minimal effective amount that enables the determination of the inhibition of a biochemical marker associated with the immunoplastic tissue of interest. It is theoretically possible, though presently not proven, to saturate the receptor sites with the initial dose of unlabeled somatostatin congener which would make the second labeled dose superfluous. Thus, the initial dose of unlabeled somatostatin congener should be limited to a biochemical marker-inhibiting dose. Since the biochemical marker typically will be assayed in order to confirm the suspected presence of neoplastic tissue, the level of such biochemical marker will be determined prior to the initial dose administration. The amount of inhibition necessarily will depend upon the level initially determined in the patient as well as the amount of unlabeled congener administered to the patient.

Once the ability of the somatostatin congener to associate with the neoplastic tissue has been confirmed, the patient can be scheduled for surgery in appropriate fashion. As the examples reveal, the ability to detect and differentiate neoplastic tissue from surrounding healthy tissue can be realized in as short a time as 15 to 60 minutes following administration of the radiolabeled somatostatin congener. Thus, it is possible to administer the labeled congener to the patient upon his or her entry into the operating room since typical cancer surgical procedures are of multiple hour duration. The ability to detect such neoplastic tissue several hours following administration, however, also has been confirmed which provides extra flexibility for the surgeon in planning the procedure.

With respect to the radiolabel of choice, the ability to use a radiation detection probe that can be placed in immediate adjacency to the neoplastic tissue means that lower level energy isotopes are preferred, especially those exhibiting photon emissions of energy levels less than about 300 kev advantageously and preferably less than about 150 kev. $^{125}$I currently is the isotope of choice, though additional low energy isotopes as disclosed in the '840 patent may be used as is necessary, desirable, or convenient. Higher energy level radioisotopes (e.g., $^{131}$I) also may be used, though suitable collimation of the radiation detection probe must be employed which may impede the instrument being facile to the surgeon and limit the areas within the body cavity which can be suitably surveyed.

In addition to radioisotopes emitting gamma radiation, radioisotopes exhibiting beta radiation additionally can be used in conjunction with a probe which can detect beta radiation or positrons. The detection of beta radiation intraoperatively is disclosed, for example, in U.S. Pat. No. 5,008,546, the disclosure of which is expressly incorporated herein by reference.

Two different commercially available tyrosinated somatostatin congeners have been tested in accordance with the present invention. Both are cyclic octapeptide analogues of somatostatin with a tyrosine in the third position, and both afforded excellent results. One is Tyr$^3$-octreotide or SDZ 204–090, a derivative of Sandostatin® or SMS 201–995 (Sandoz Pharma, Ltd., Basel, Switzerland); the other is lanreotide or Somatuline® (Biomeasure, Inc., Milford, Mass. U.S.A.).

Tyr$^3$-octreotide can be labeled with $^{125}$I using a modification of Reubi's chloramine-T technique. To a vial containing 2.0 mCi (milli-Curies) of $^{125}$I is added 0.1 mL of 0.5 M potassium/sodium phosphate buffer, pH 7.5, and the contents mixed well. Next, 10 µg of Tyr$^3$-octreotide in 0.1 mL of 0.05N acetic acid is added to the vial and the contents mixed well. Rapidly and in turn to the vial are added 11.3 µg (micrograms) of chloramine-T (10 µliters), and after a 60 second delay, 113 µg of sodium metabisulfite (100 µliters) to terminate the reaction. One-minute reaction times are used. Each step is continually bounce-mixed to ensure rapid and proper mixing. The 330 µL reaction volume is transferred to the top of a dry cellulose column bed to separate the iodinated peptide from free iodine.

A Whatman CF-1 cellulose powder column is washed with 20 mL of 0.05M potassium/sodium phosphate buffer, pH 7.5, and eluted with 0.2N acetic acid containing 10% deproteinized serum. Three 5-mL wash buffer fractions are collected in tubes numbered 1–3, and 27 1-mL buffer fractions are collected in tubes numbered 4–30. Ten microliters from each fraction is transferred to a correspondingly marked 10×75 mm glass tube, and counted for 0.1 second by a gamma radiation counter. The fractions with the highest counts (usually fractions 10–22) are pooled.

A SEP-PAK C$_{18}$ cartridge (Waters Associates, Part No. 51910) is sterilized with 5 mL of 70% ethanol and activated with 5 mL of 2-propanol followed by 12.5 mL of high performance liquid chromatography (HPLC) water. The pooled fractions are applied to the cartridge and eluted immediately. First, the column is washed with 5 mL of HPLC water, then with 5 mL of 0.05M acetic acid, and eluted with 5 mL of 96% ethanol. The eluate is collected in a 16×100 mm glass tube. HPLC purification involves evaporation of the eluate in 96% ethanol to dryness in a 40° C. water bath using a gentle flow of nitrogen. The dried residue is reconstituted with 0.2 mL of 27:73 acetonitrile/35 mM ammonium fore, ate (pH 3.0) and incubated at 40° C. for 5 minutes to ensure complete reconstitution (intermittent mixing on a vortex during incubation). The redissolved Tyr$^3$-octreotide is loaded on the HPLC for further purification. The flow rate is 1 mL/min. for 15 minutes wherein thirty 0.5 mL fractions are collected. Again, 10 µL from each fraction is transferred to a correspondingly marked 10×75 mm glass tube and counted for 0.1 sec. on a gamma radiation counter. The purified $^{125}$I Tyr$^3$-octreotide elutes off the column in 7 minutes. The best $^{125}$I Tyr$^3$-octreotide fraction is selected and evaporated to dryness in a 40° C. water bath using a gentle flow of nitrogen. The dried residue then is reconstituted with 0.5 mL of 0.9% NaCl in 0.05 M HOAc. Finally, the solution is passed through a low protein-binding 0.22 micron Millex-GV filter and administered to the patient intravenously.

Lanreotide, or Somatuline®, can likewise be radiolabeled with $^{125}$I using a modification of Reubi's chloramine-T technique. The $^{125}$I to be used is first vented with a charcoal filter. Forty mg of chloramine-T is dissolved in 100 mL of 0.05M potassium/sodium phosphate buffer, pH 7.5, ten minutes prior to use. Also at this time 40 mg of sodium metabisulfite is dissolved in 100 mL of identical potassium/ sodium phosphate buffer. Next, 170 L of the potassium/ sodium phosphate buffer is added to a vial holding 2.0 mCi of $^{125}$I in 20 L of buffer. To this vial is added 30 of Somatuline® in 50 mL of 0.1M sodium acetate, pH 4.5, and the contents are mixed thoroughly. Added to the vial, rapidly and in turn with continuous bounce-mixing, are 10 mL of chloramine-T and, following a 60-second delay, 100 mL of sodium metabisulfite to terminate the reaction. A 90-second reaction time is allowed.

The 330 mL reaction volume is transferred to the top of a dry cellulose column bed to separate the iodinated peptide from free iodine. From this point on, the procedure followed is identical to that described for the radiolabeling of Tyr$^3$-octreotide, supra. Reconstitution and filtering yield a radiolabeled congener of high affinity and high purity ($K_d$=1.32 nM, $B_{max}$=0.22 nM, IMR32 neuroblastoma cell membranes).

The dosage of labeled peptide is such that the radiation detection probe can be utilized for determining tumor sites exhibiting accretion of the radiolabeled somatostatin congener. Such dosages depend upon the specific type of label, the type of congener, and like factors which may affect dosage requirements as those skilled in the art will appreciate. Currently, clinical use of octreotide acetate reveals dosages ranging from about 300 to 1,500 µg per day, though lower dosages, say 100 µg, ultimately may prove efficacious.

The primary biochemical marker mediated by the administered unlabeled somatostatin congener should exhibit a decrease of at least about 20%, advantageously about 30%, and preferably 50% reduction in marker, as evidence that the labeled congener will bind to the cell membrane receptors and be detectable in vivo during surgery for cytoreduction of the tumor.

With respect to the radiolabel, delivered doses from about 0.03 to 1 mCi of $^{125}$I have been used in clinical studies and have been found to be detectable at the tumor site. Delivered dosages of the somatastatin congener (radiolabeled) ranges from about 0.1 ng to 10 µg broadly and about 0.5 ng to 1 µg advantageously. Thus, though both the amount of radiolabel and the amount of congener delivered to the tumor are small, in situ in vivo detection thereof still is quite practical.

With respect to the detection of tumor sites exhibiting accretion of the radiolabeled somatostatin congener, reference is made to the following patents which show a preferred hand-held probe for the detection of gamma radiation: U.S. Pat. Nos. 4,801,803, 4,889,991, and 5,070,878, the disclosures of which are expressly incorporated herein by reference. As stated above, U.S. Pat. No. 5,008,546 discloses a probe suitable for the detection of beta radiation. Additional radiation detection devices can be used as is necessary, desirable, or convenient. In this regard, it will be appreciated that intraoperative accession of the patient in order to determine neoplastic tissue is but one alternative for practice of the present invention. Additionally, probes may be used as part of an endoscope, laparoscope, or like specific instrument (e.g., bronchoscope or like instrument) which suitably can be outfitted with a miniaturized radiation detection device which can be placed immediately adjacent the neoplastic tissue in order to determine accretion of radioactivity. Regardless of the instrument or technique employed, the present invention encompasses all such instruments and techniques, by whatever label.

The following Examples show how the present invention has been practiced, but should not be construed as limiting. In this application, all citations are expressly incorporated herein by reference.

EXAMPLE 1

In characterizing the animal model, a cell line (IMR32) expressing high affinity somatostatin receptors in cell culture was injected into the flanks of nude mice (3×10$^7$ cells/ animal). When tumors reached the palpable stage (approximately 180 days), the mice were injected peritoneally with 10 mCi of $^{125}$I-Tyr$^3$-octreotide. The heart, opposite flank, and tumor site were then monitored with a Neoprobe® RIGS® model 1000 portable radiation detector (Neoprobe Corporation, Columbus, Ohio U.S.A.).

The same procedure was followed except that the SKNSH cell line was substituted for the IMR32 cell line. The SKNSH cell line demonstrates receptor expression by RTPCR, but not by classical binding studies. With this cell line, tumors were more rapidly palpable, approximately 33 days post injection.

Figure 1B:
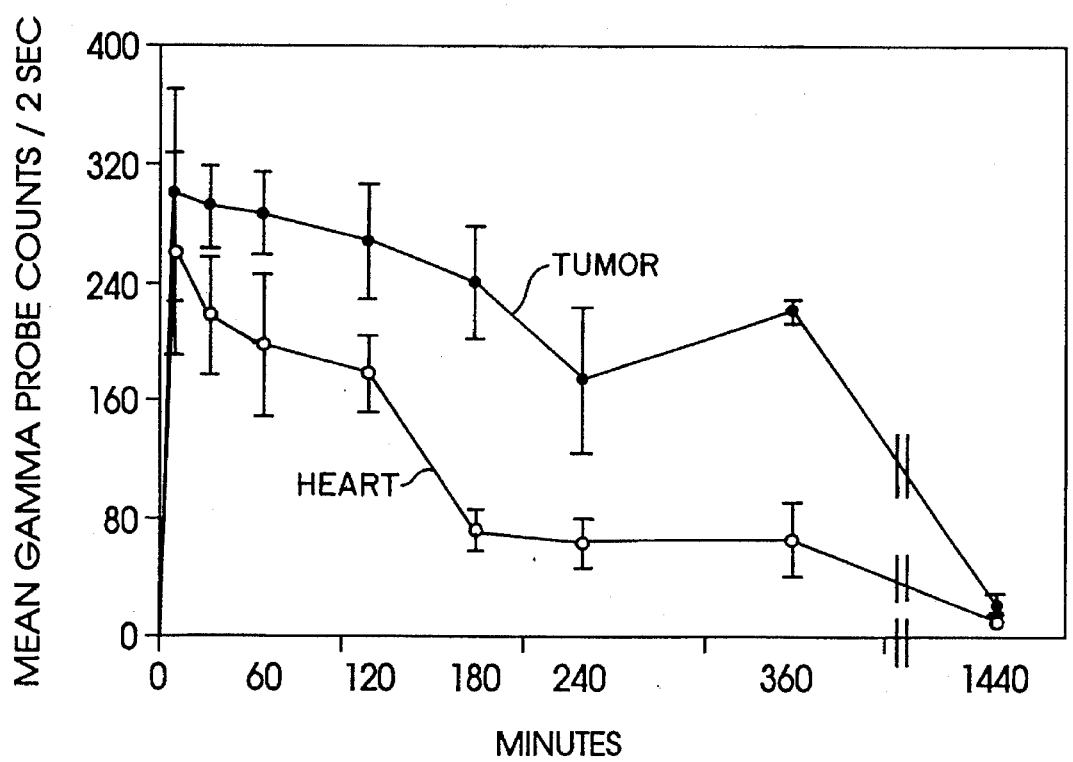

As shown in Table 1, increased uptake of $^{125}$I-Tyr$^3$-octreotide was observed in both IMR32 and SKNSH tumors, suggesting that in vivo binding is more sensitive than classical in vitro binding techniques. The percent of injected radioactivity taken up in normal tissues of the nude mouse is shown in Table 2. The tumor uptake compared to the blood pool is depicted graphically in FIGS. 1a and 1b. These results demonstrate increased radioactivity in tumor tissue compared to surrounding normal tissue, thus suggesting that this radiolabeled ligand would be useful in detecting human tumors in vivo.

TABLE 1

IN VIVO RADIORECEPTOR ASSAY IN
XENOGRAFT MODEL
MEAN GAMMA PROBE COUNTS

| Min. After Inject. | IMR 32 | | SKNSH | |
|---|---|---|---|---|
| | BLOOD | TUMOR | BLOOD | TUMOR |
| 1 | (4)151.3 | 447.6 | (4)167.2 | 273.4 |
| 30 | (4)216.7 | 292.2 | (0)— | — |
| 60 | (4)197.0 | 287.1 | (4)86.2 | 181.1 |
| 120 | (4)177.6 | 268.3 | (5)85.3 | 165.6 |
| 180 | (4)71.6 | 239.8 | (5)56.6 | 121.8 |
| 360 | (3)66.2 | 220.0 | (0)— | — | n = ( )

TABLE 2

ACCUMULATION OF $^{125}$I-OCTREOTIDE IN NUDE
MOUSE TISSUES
(% Injected Dose per Organ)

| Tissue | 10 Min. (N = 2) | 30 Min. (N = 2) | 60 Min. (N = 1) | 180 Min. (N = 1) | 240 Min. (N = 3) | 360 Min. (N = 2) |
|---|---|---|---|---|---|---|
| Liver | 4.70(1.8)* | 5.07(3.5) | 3.03 | 1.33 | 1.62(1.7) | 1.80(1.1) |
| Spleen | 0.50(0.3) | 0.20(0.1) | 0.10 | 0.03 | 0.07(0.03) | 0.16(0.1) |
| Kidney | 0.95(0.03) | 1.18(0.4) | 1.36 | 0.62 | 1.25(0.9) | 1.61(0.6) |
| Blood | 0.76(0.5) | 1.37(1.5) | 0.71 | 0.19 | 0.32(0.5) | 0.25(0.4) |
| Small Bowel | 1.91(0.1) | 3.13(1.1) | 3.98 | 1.56 | 0.83(0.4) | 2.51(1.9) |
| Large Bowel | 0.75 90.3) | 0.72(0.2) | 3.80 | 6.36 | 3.13(3.5) | 6.90(6.1) |
| Muscle | 0.20(0.1) | 0.09(0.1) | 0.10 | 0.01 | 0.02(0.02) | 0.04(0.03) |
| Vertebrae | 0.61(0.7) | 0.44(0.5) | 0.14 | 0.07 | 0.07(0.09) | 0.08(0.05) |
| Pancreas | 0.77(0.4) | 0.40(0.5) | 0.48 | 0.06 | 0.17(0.1) | 0.15(0.01) |
| Brain | 0.01(0.01) | 0.02(0.01) | 0.02 | 0.01 | 0.02(0.02) | 0.03(0.01) |
| Thyroid | 0.24(0.3) | 0.19(0.2) | 0.03 | 0.01 | 0.04(0.04) | 0.04(0.04) |
| Lung | 0.38(0.3) | 0.65(0.7) | 0.28 | 0.10 | 0.26(0.2) | 0.34(0.004) |
| Heart | 0.19(0.2) | 0.17(0.16) | 0.09 | 0.02 | 0.06(0.07) | 0.07(0.03) |
| Adrenal | 0.13(0.12) | 0.06(0.07) | 0.03 | 0.01 | 0.01(0.01) | 0.01(0.001) |
| Stomach | 4.32(3.0) | 5.64(4.5) | 3.33 | 1.38 | 3.88(1.9) | 1.50(0.7) |
| Gallbladder | 4.56(3.8) | 2.2(1.7) | 1.41 | 0.34 | 0.83(1.0) | 0.74(0.2) |

*( ) indicates SD

EXAMPLE 2

Figure 2D:
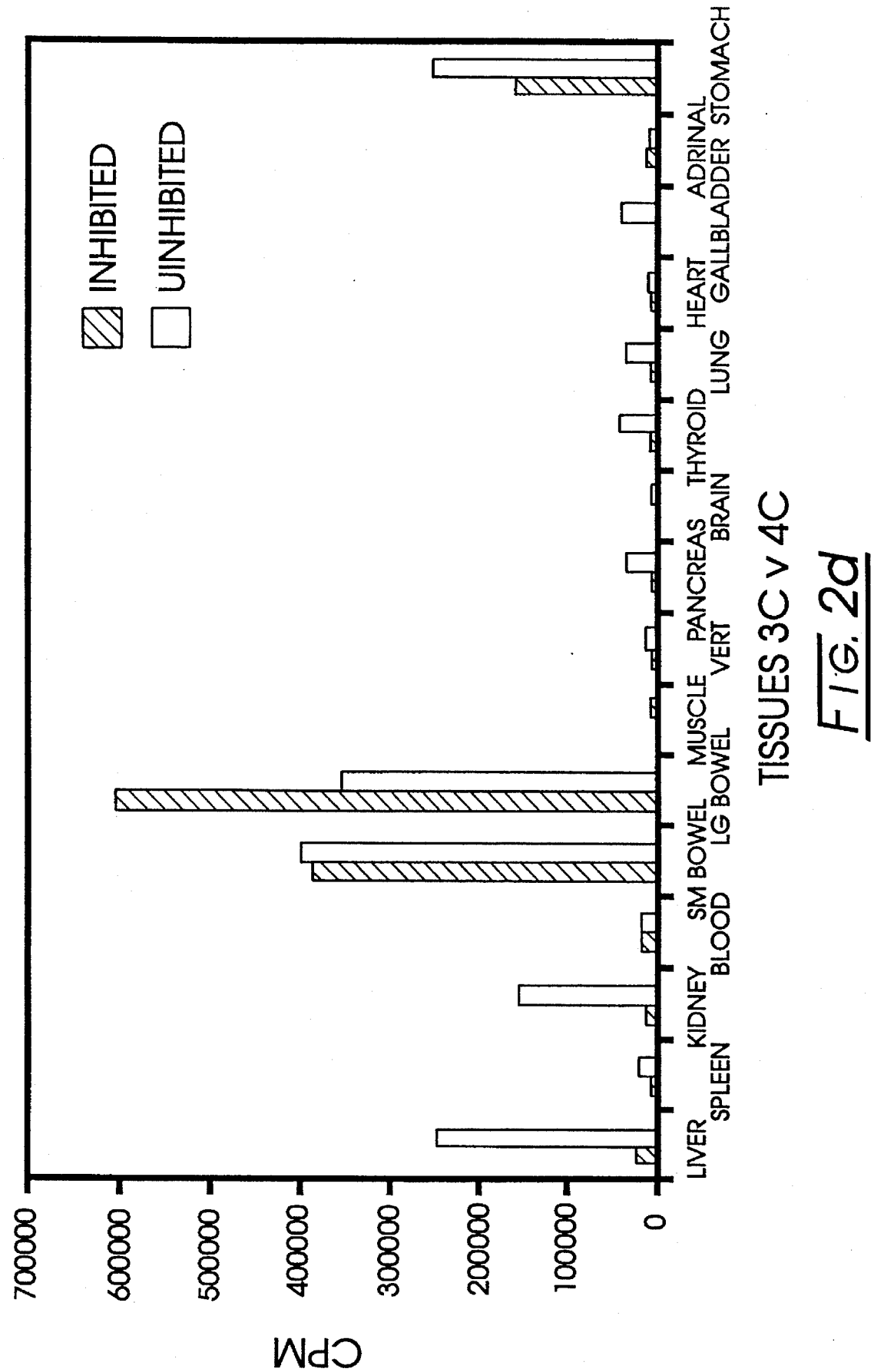
FIG. 2 compares in vivo and ex vivo counts obtained at two different time intervals in paired animal populations, in order to demonstrate the effect of nonspecific binding of $^{125}I$-$Tyr^3$-octreotide.

The specificity of in vivo $^{125}$I-Tyr$^3$-octreotide binding was studied in non-tumor-bearing nude mice. Paired animals received an intraperitoneal injection of 20 mCi (0.016 ng) $^{125}$I-Tyr$^3$-octreotide. One animal in each pair received 16 ng of unlabeled Tyr$^3$-octreotide 5 minutes prior to injection of $^{125}$I-Tyr$^3$-octreotide. Key organs were probed with the Neoprobe® RIGS® model 1000 portable radiation detector in the intact animal at either 5 minutes or 6 hours after the injection of $^{125}$I-Tyr$^3$-octreotide. Counts after 5 minutes are shown in FIG. 2a; those after 6 hours are shown in FIG. 2b. The animals were then immediately sacrificed, and the organs were excised, weighed, and counted in a gamma counter. Whole organ counts after 5 minutes are shown in FIG. 2c; those after 6 hours are shown in FIG. 2d. The uptake of $^{125}$I-Tyr$^3$-octreotide in those animals which received 16 ng of unlabeled Tyr$^3$-octreotide should provide an estimate of nonspecific binding, including radioactivity being transported in the blood vessels of the tissue being measured. Subtraction of this "nonspecific binding" in one animal from the total radioactive uptake in the paired animal which received only $^{125}$I-Tyr$^3$-octreotide (total binding) should provide an estimate of specific binding in any given tissue.

A good correlation in tissue specific binding is seen between the Neoprobe® radiation detector counts (FIGS. 2a and 2b) and the whole tissue counts following tissue excision (FIGS. 2c and 2d). The difference in scale between the Neoprobe® radiation detector counts, taken for 2-second intervals over an area of tissue 2 mm in diameter, and the whole tissue counts, taken ex vivo in a gamma counter, should be noted. Both the in vivo Neoprobe® counts and the ex vivo whole organ counts clearly demonstrate specific uptake of $^{125}$I-Tyr$^3$-octreotide in the liver, spleen, and kidney at 5 minutes, but no specific binding in blood. In other words, nonspecific (inhibited) binding exceeds total (uninhibited) binding. Other tissues which demonstrated specific binding at 5 minutes included the small and large bowel and the pancreas, but not the muscle, brain, thyroid, gall bladder, or stomach.

At 6 hours, there was a good correlation between in vivo Neoprobe® radiation detector counts and ex vivo whole organ counts in terms of which tissues demonstrated specific binding. Specific uptake was seen at 6 hours in liver, spleen, kidney, but not in blood, small bowel, or large bowel. At 6 hours specific binding was observed in stomach. The tissues which demonstrated specific binding by this in vivo radioreceptor assay correlated extremely well with recent publications regarding tissue-specific expression of somatostatin receptor mRNA in various tissues (Yamada et al., "Cloning and Functional Characterization of a Family of Human and Mouse Somatostatin Receptors Expressed in Brain, Gastrointestinal Tract, and Kidney," *Proc. Natl. Acad. Sci.*, 1992, 89: 251–255; Yamada et al., "Somatostatin Receptors, an Expanding Gene Family: Cloning and Functional Characterization of Human SSTR3, a Protein Coupled to Adenylyl Cyclase," *Mol. Cell Endocrinol.*, 1992, 6: 2136–2142), thus supporting the validity of in vivo somatostatin receptor binding using $^{125}$I-Tyr$^3$-octreotide.

This and the previous Example provide a very strong rationale for the use of $^{1251}$Tyr$^3$-octreotide Neoprobe® gamma radiation detection intraoperatively, even in patients whose tumors do not demonstrate high affinity binding in vitro.

EXAMPLE 3

The patient (VS) was a 61-year-old white female who had undergone pancreatoduodenectomy in 1989 for a glucagonoma of the pancreas. She developed symptomatic recurrence in the interim, and underwent a repeat abdominal exploration wherein a residual tumor was found and resected. Recent symptoms include recurrent abdominal pain, nausea, and vomiting. Preoperative workup demonstrated a recurrent mass in the area of the head of the pancreas consistent with recurrent tumor. Additionally, the patient had an upper gastrointestinal series which demonstrated ulcerations and edema in the area of the gastrojejunostomy. A diagnosis of bile reflux gastritis with marginal ulceration was made. A 13-hour external scan with 5.3 mCi of $^{123}$I-Tyr$^3$-octreotide demonstrated equivocal uptake in the area of this pancreatic mass.

Figure 3:
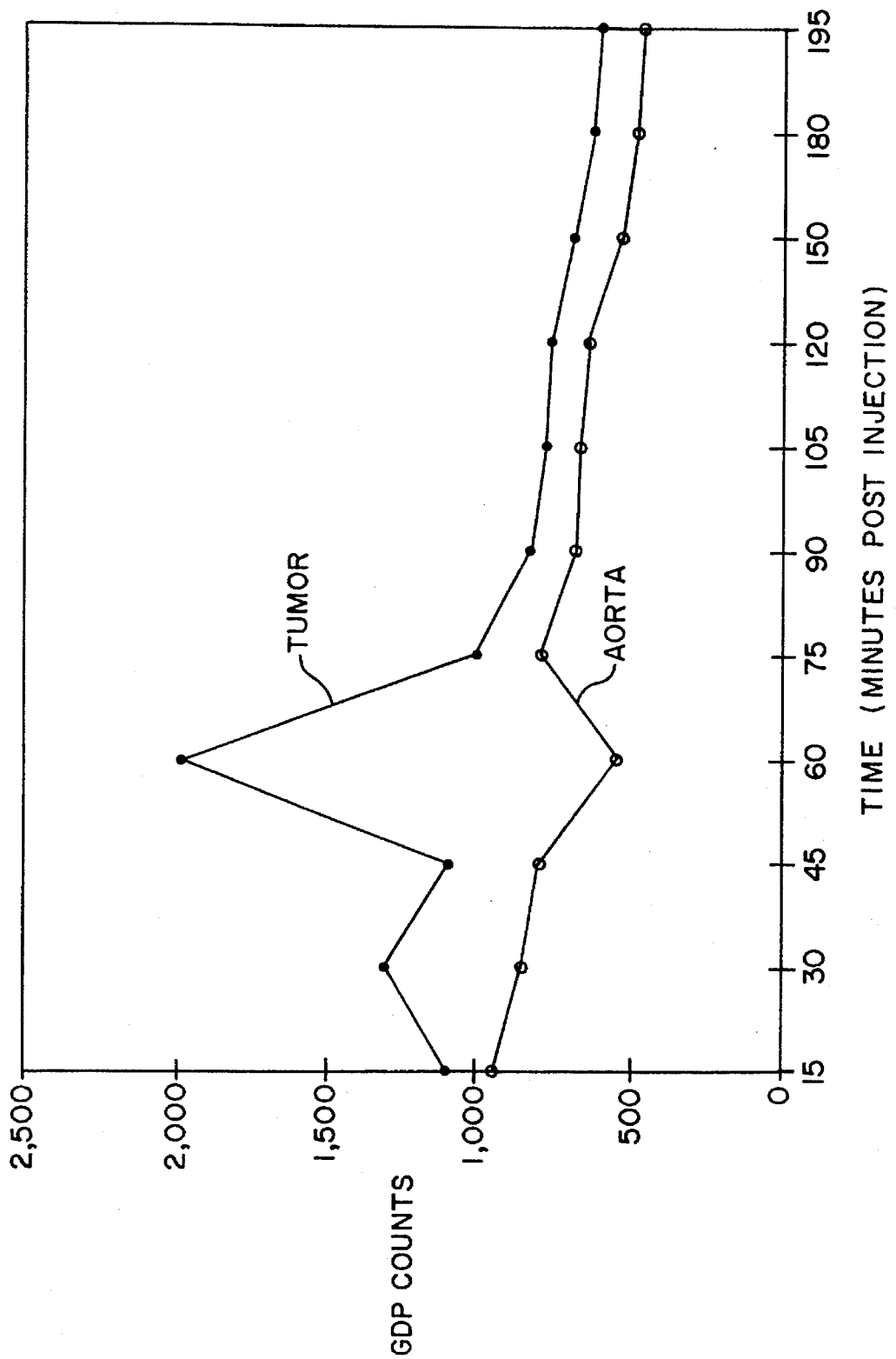
FIGS. 3–10 graphically display the counts evidenced by diseased (neoplastic) tissue containing somatostatin receptors and adjacent healthy tissue versus time post-injection of $^{125}I$-$Tyr^3$-octreotide in several human patients.

Six days later, the patient was taken to surgery and the mass visualized. Thereafter, the patient was administered 347 µCi of $^{125}$I-Tyr$^3$-octreotide and scanned with a Neoprobe® RIGS® model 1000 portable radiation detector. The counts of the tumor and adjacent aorta are displayed graphically versus time post-injection in FIG. 3. Gamma probe counts are given in Table 3. It will be seen that at about one hour post injection a large uptake of $^{125}$I-Tyr$^3$-octreotide is evident; however, little differentiation of counts is apparent thereafter. It is surmised that the one-hour peak of radiation is due to neovascularization by the tumor.

The surgical results were consistent with the pre-operative testing, confirming that the tumor did not possess sufficient somatostatin receptors to make uptake of labeled octreotide a viable tool in determining neoplastic tissue in this patient.

TABLE 3

| | MEAN GAMMA PROBE COUNTS/2 SEC. | | | | | | | |
|---|---|---|---|---|---|---|---|---|
| Site | 15 | 30 | 45 | 60 | 75 | 90 | 105 | 120 |
| Pancreatic Tumor | 1076 | 1307 | 1005 | 1973 | 1398 | 765 | 771 | 754 |
| Aorta | 947 | 848 | 792 | 539 | 787 | 671 | 659 | 632 |

EXAMPLE 4

The patient (CT) was a 52-year-old white female that complained of nonspecific abdominal pain. Upon challenge with 100 µg of unlabeled octreotide acetate, the level of gastrin-releasing peptide (GRP) dropped from 10,500 to 297 pg/mL. This drop is indicative that the somatostatin congener administered is binding to somatostatin receptors associated with the tumor.

Figure 4:
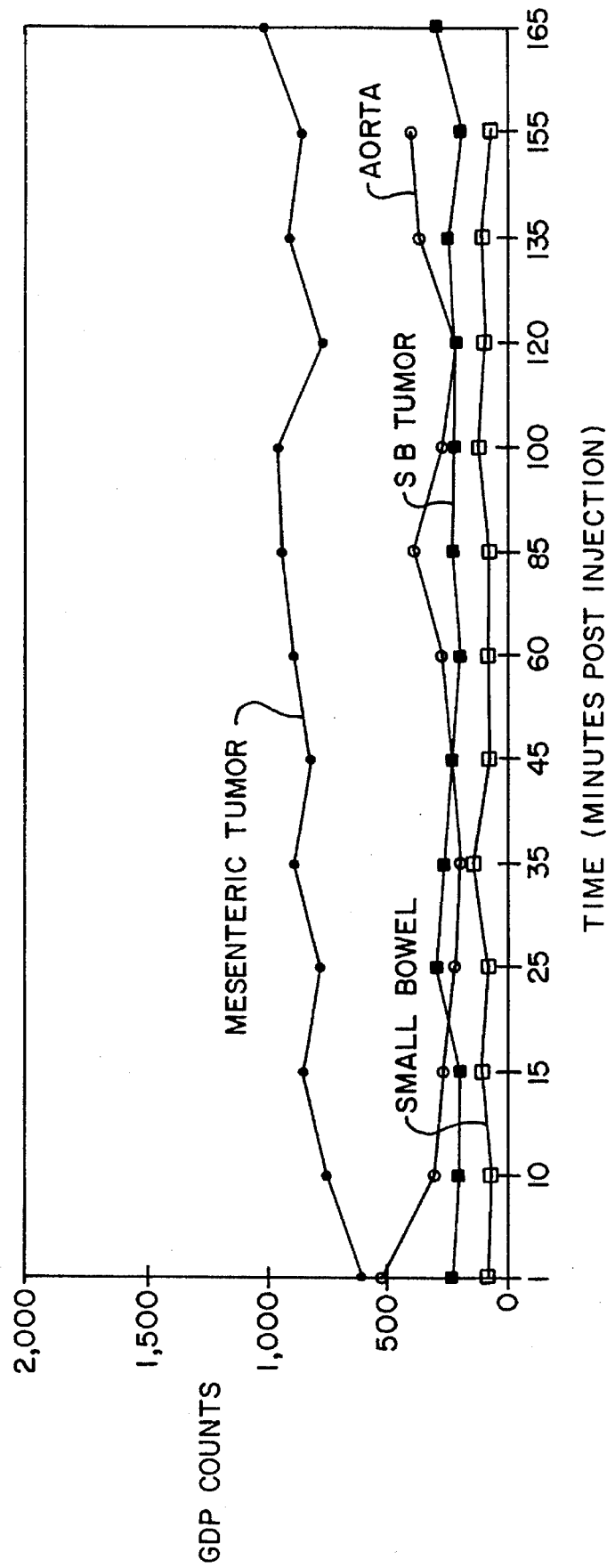

At the time of surgery, the patient was administered 195 µCi of $^{125}$I-Tyr$^3$-octreotide and scanned as described in Example 3. The results of the intraoperative probing are displayed graphically in FIG. 4 and in tabular form in Table 4. It will be observed that the mesenteric nodal tumor evidenced counts well above the adjacent aorta. In addition, the primary small bowel tumor had uptake consistently two-fold of that adjacent normal and uninvolved small bowel tissue. These results are indicative of the presence of somatostatin receptors both within the primary small bowel tumor and its metastatic deposits.

After resection of all gross tumor, the remainder of the abdomen was scanned to search for occult malignancy. Several lymph nodes posterior to the pancreas and around the celiac axis probed positive. These were excised and proved to contain metastatic carcinoid tumor. In essence, the probe facilitated tumor detection and led to more effective cytoreduction.

TABLE 4

| | INTRAOPERATIVE GAMMA PROBE COUNTS/2 SEC. | | | | |
|---|---|---|---|---|---|
| Minutes Post-injection | Aorta | Mesenteric Tumor | Small Bowel Tumor | Small Bowel | Liver |
| 1 | 520 | 596 | 229 | 82 | 898 |
| 10 | 303 | 755 | 203 | 66 | 1082 |
| 15 | 268 | 849 | 200 | 105 | 1564 |
| 25 | 218 | 775 | 294 | 79 | 1518 |
| 35 | 194 | 886 | 261 | 1459 | 1543 |
| 45 | 229 | 816 | 229 | 76 | 1651 |
| 60 | 269 | 888 | 192 | 80 | 1827 |
| 85 | 386 | 936 | 226 | 75 | 1399 |
| 100 | 271 | 953 | 222 | 122 | 1177 |
| 120 | 197 | 764 | 223 | 95 | 1633 |
| 135 | 360 | 905 | 247 | 104 | 1153 |
| 155 | 395 | 849 | 187 | 72 | 1026 |
| 165 | | 1011 | 295 | | |
| Average Cts. | 200.8 | 844.8 | 231.4 | 91.2 | 1372.6 |
| Median Cts. | 270 | 849 | 226 | 81 | 1458.6 |
| Stand. Dev. | 93.5 | 102.7 | 33.5 | 22.5 | 282.2 |
| Range | 194–520 | 596–1101 | 187–295 | 66–145 | 897–1827 |

EXAMPLE 5

The patient (RT) was a 52-year-old white female who, upon evaluation of her intractable recurrent peptic ulcer disease, was found to have high gastrin levels. Further evaluation including gastric acid studies and provocative testing with secretin was consistent with a gastrin-producing tumor. Despite an arteriogram, abdominal CT, upper endoscopy, and nuclear medicine localization scan, the location of the gastrinoma was unknown. The patient had an elevated gastrin level as well as an elevated pancreatic polypeptide level. Sixty minutes following subcutaneous challenge with 100 mcg of unlabeled octreotide, gastrin fell from 174 pg/mL to 100 pg/mL (37% reduction) and pancreatic polypeptide from 532 pg/mL to 118 pg/mL (88% reduction) after 60 minutes. It is believed that a 50% reduction in an elevated tumor peptide marker predicts the presence of somatostatin receptors on the tumor cells and, therefore, may also predict the potential success of localization with the probe.

Figure 5:
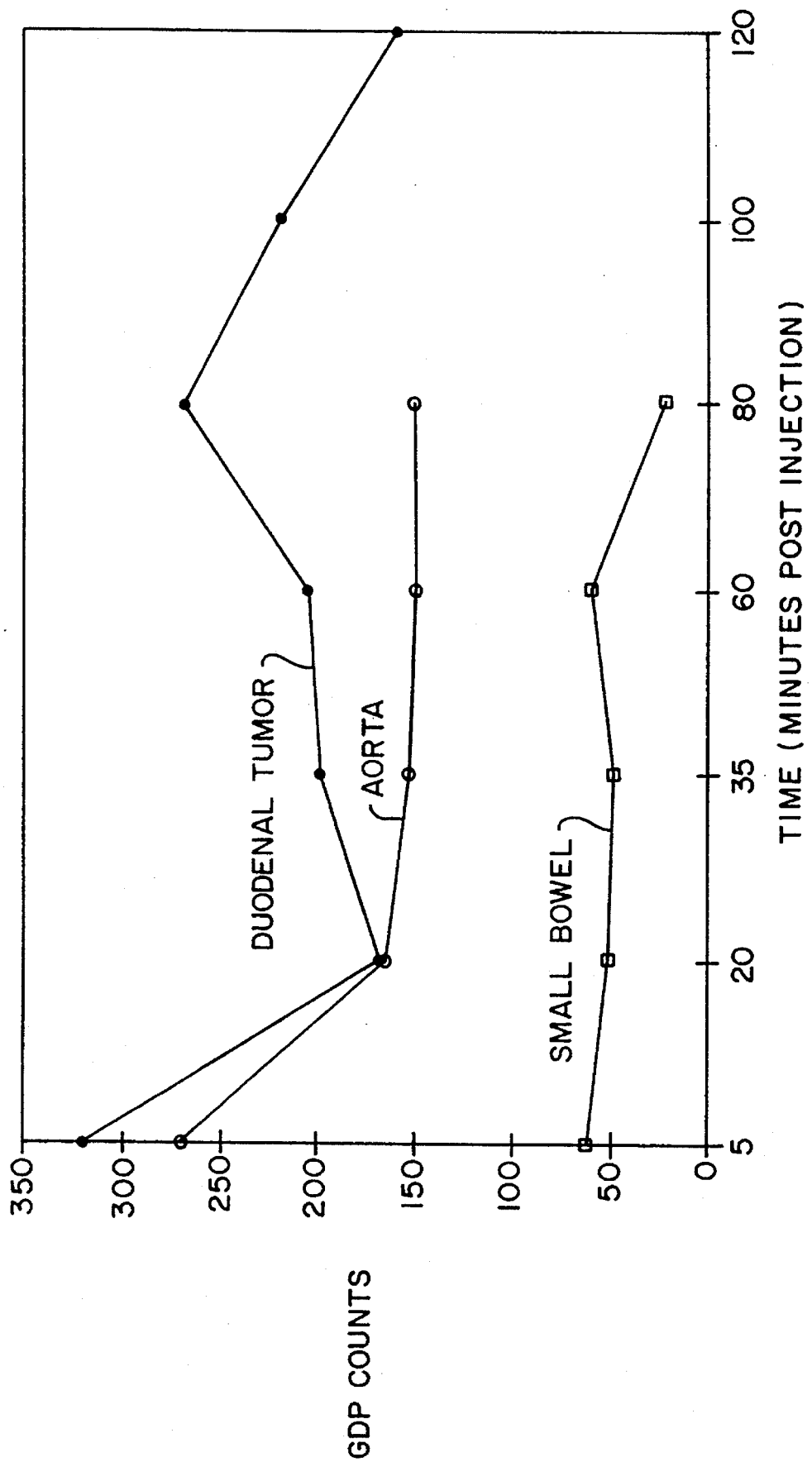

At surgery, a gross visual and manual inspection showed no sign of tumor in the patient's liver. Additionally, her stomach, pancreas, pelvis and ovaries evidenced no abnormalities. The gastrohepatic ligament was carefully palpated with similar findings. Her retroperitoneal area, after extensive Kocherization maneuver, appeared to be within normal limits. The entire course of the pancreas was imaged using intraoperative ultrasonography and appeared normal. The patient thereupon was injected with 223 µCi $^{125}$I-Tyr$^3$-octreotide and probe counts taken, as described above and listed in Table 5. The results are displayed graphically in FIG. 5.

The probe seemed to indicate increased octreotide uptake in the duodenal bulb when compared to the more distal duodenum. The duodenum was opened in the region of the high signal and a submucosal nodule was found. Pathology revealed a gastrinoma. Because of the invasive appearance of the tumor on frozen section, a formal pancreatoduodenectomy was carried out. Two lymph nodes containing microscopic foci of metastatic tumor were found in the final specimen. The patient's post-operative gastrin level is 42 pg/mL and she remains asymptomatic. The case clearly illustrated the ability of the probe to detect occult tumor foci not detectable by conventional imaging modalities.

TABLE 5

INTRAOPERATIVE GAMMA PROBE COUNTS/2 SEC.
TIME IN MINUTES

| Site | 5 | 20 | 35 | 60 | 80 | 100 | 120 |
|---|---|---|---|---|---|---|---|
| Aorta | 270 | 160 | 150 | 148 | 150 | — | — |
| Small Bowel | 67 | 50 | 48 | 59 | 20 | — | — |
| Duodenal Tumor | 270 | 168 | 199 | 205 | 263 | 213 | 157 |

EXAMPLE 6

Figure 6A:
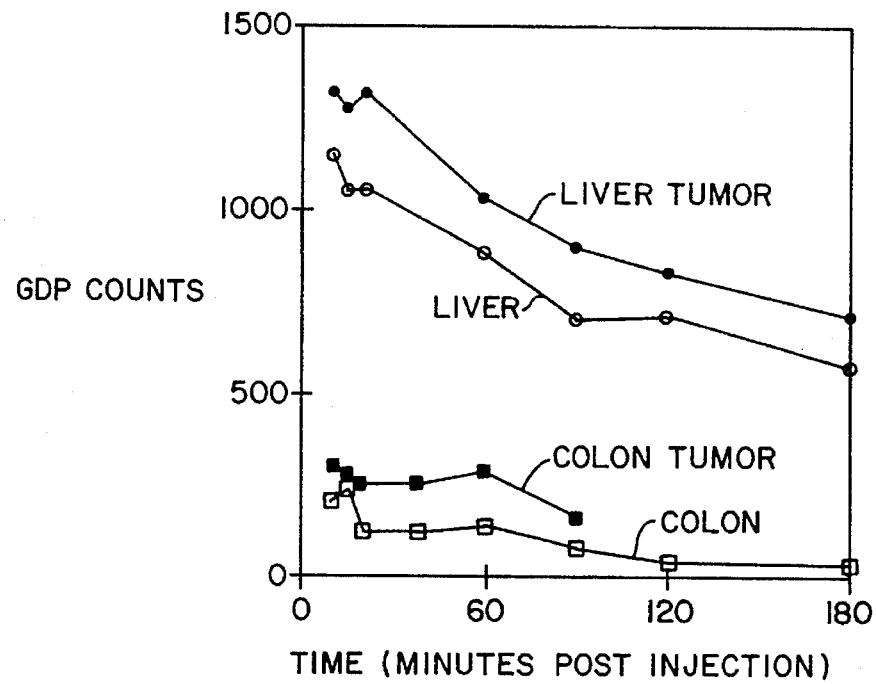
Figure 6B:
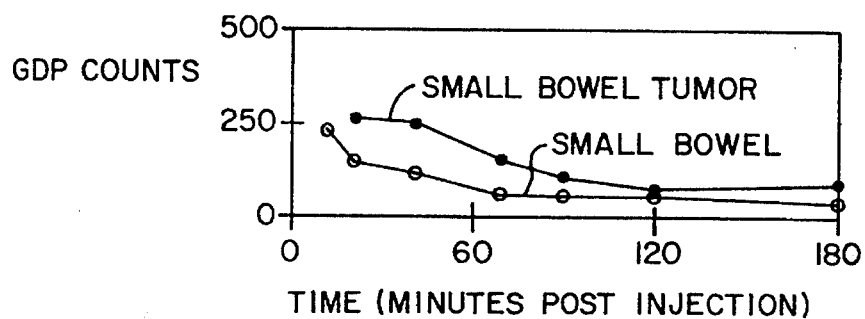
Figure 6C:
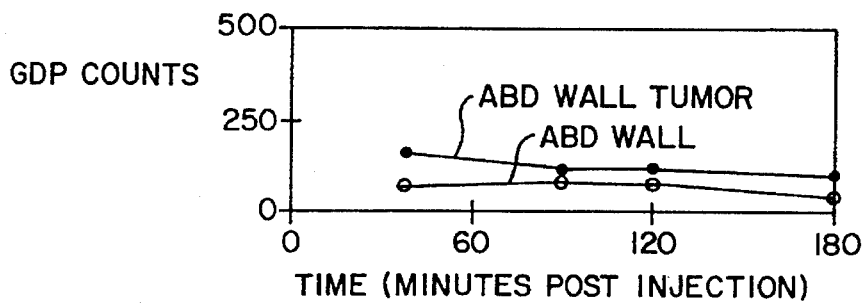
Figure 6D:
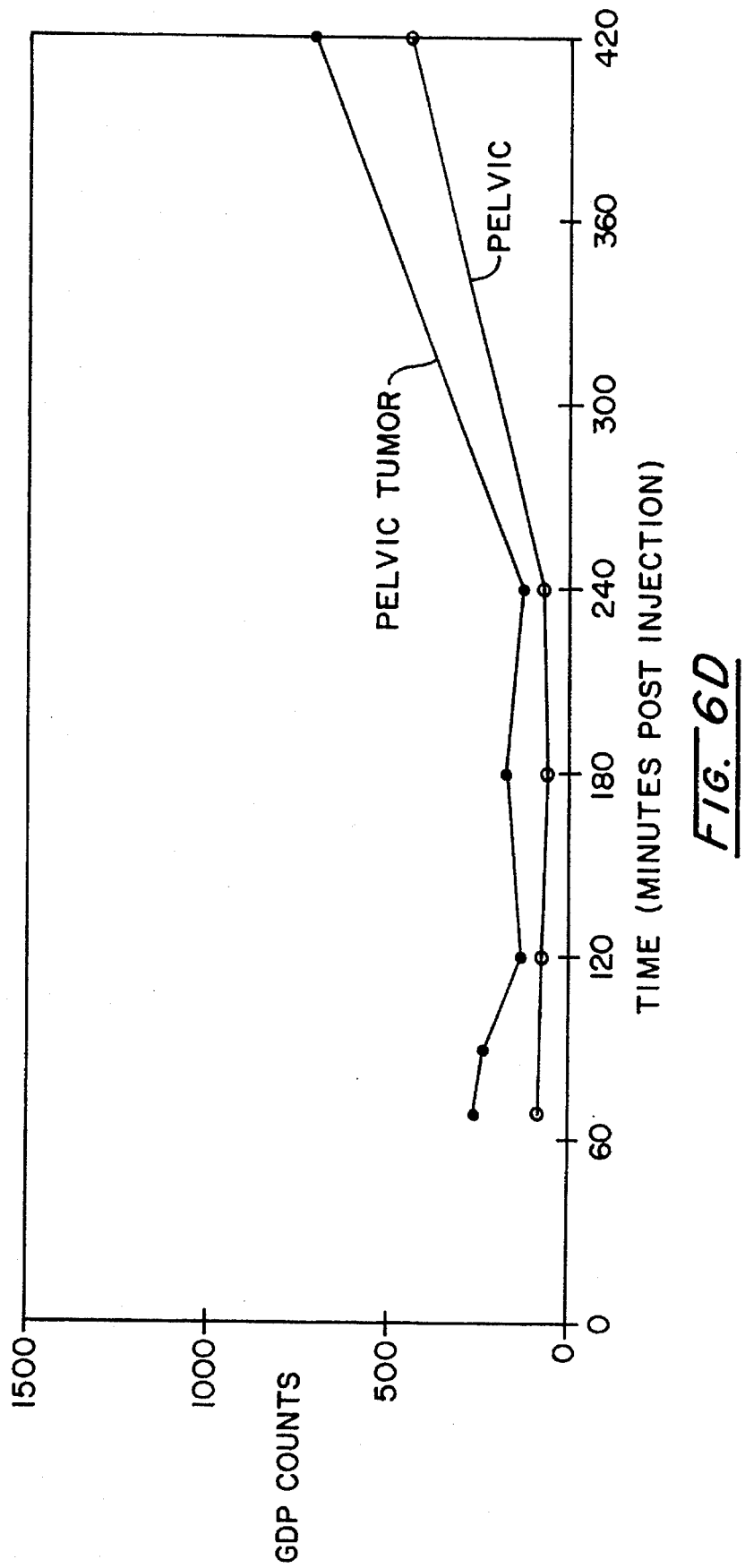

The patient (SR) was a 50-year-old white female with a history of carcinoid. In July 1990, she had had a jejunal resection with 5-FU administered thereafter. In the interim, she experienced intermittent vomiting, abdominal pain, and flushing. Elevated serotonin levels of 217 in October 1990, and 484 in January 1991, led to her readmittance for surgery. Administration of 50 µg of unlabeled octreotide led to a decrease in serotonin level. An exploratory laparotomy was performed. At the time of surgery, the patient was injected with 153 µCi of $^{125}$I-Tyr$^3$-octreotide. The probe confirmed the suspected tumor, and pathology confirmed carcinoma. The results are displayed in Table 6 and in FIGS. 6a 6d. Besides those values displayed in FIG. 6, additional counts were taken as follows: abdominal wall implant 835 counts at 40 minutes versus abdominal wall 115 counts, and abdominal wall implant 213 counts at 4 hours versus abdominal wall 65 counts; and retroperitoneal tumor 537 counts at 70 minutes versus right iliac artery 124 counts, and retroperitoneal tumor 199 counts at 3 hours versus right iliac artery 96 counts. Surgery involved a biopsy of a bladder nodule and abdominal wall lesion with pathology confirming carcinoma by frozen section. Resection included the terminal duodenum, proximal 30 cm of jejunum, and distal 20 cm of ileum. Also performed were a subtotal colectomy, ileostomy, partial cystectomy with right ureteral reimplantation, liver biopsy, and posterior gastrojejunostomy.

TABLE 6

INTRAOPERATIVE GAMMA PROBE COUNTS/2 SEC.

| Minutes Post-Injection | Liver | Liver Tumor | Colon | Colon Tumor | Small Bowel | Small Bowel Tumor | Abd. Wall | Abd. Wall Tumor | Pelvis | Pelvic Tumor |
|---|---|---|---|---|---|---|---|---|---|---|
| 5 | 1200 | 1323 | 243 | 277 | | | | | | |
| 15 | 1185 | 1441 | 200 | 300 | | | | | | |
| 20 | 1131 | 1436 | 170 | 240 | 180 | 249 | | | | |
| 35 | 1150 | 1340 | 121 | 256 | 106 | 258 | 72 | 151 | | |
| 40 | | | | | 119 | 146 | | | | |
| 60 | 940 | 1072 | | | | | | | | |
| 65 | | | 151 | 253 | | | | | | |
| 75 | | | | | 67 | 95 | | | 95 | 251 |
| 90 | 703 | 853 | | | | | 1242 | 1243 | | |
| 105 | | | 81 | 139 | 60 | 233 | | | | |
| 120 | | | 38 | 121 | 63 | 112 | | | | |
| 125 | | | | | | | 70 | 115 | 63 | 182 |
| 160 | | | | | | | 76 | 167 | | |
| 180 | 502 | 675 | | | 40 | 89 | 29 | 104 | 43 | 144 |

EXAMPLE 7

Figure 7:
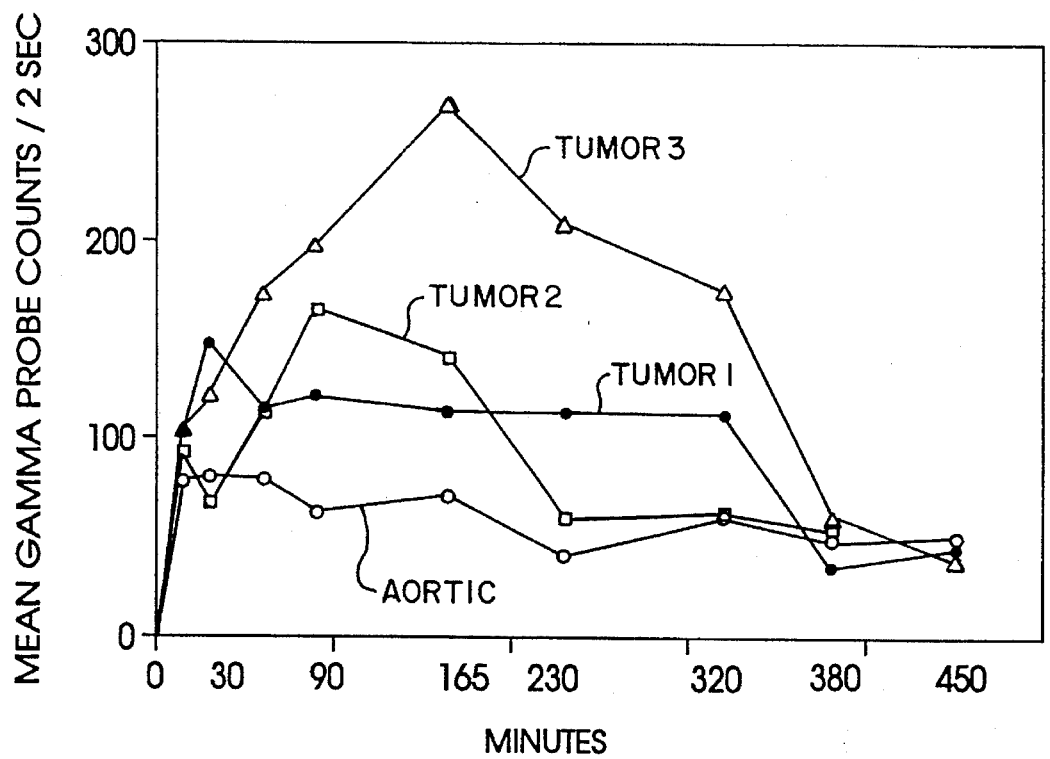

A 26-month-old white male child (AC) undergoing neuroblastoma surgery after chemotherapy was injected with 30 mCi of $^{125}$I-Tyr$^3$-octreotide upon arrival in the operating room. The time course of radioactivity in three large tumor foci in this patient is presented in FIG. 7, and in normal tissue in Table 7. These data demonstrate that the radiolabeled somatostatin congener can be injected "on the table" and the Neoprobe® RIGS® model 1000 portable radiation detector utilized to detect tumor tissue within 15 minutes. As can be seen from the time course in this patient, the tumor tissue remains above background for at least four hours. Radioactivity in the surrounding area of each tumor focus returned to normal tissue baseline counts when that particular tumor was extirpated. Histology confirmed neuroblastoma in each of the three tumors. Two occult tumor foci were also identified by the probe, as shown in Table 8.

TABLE 9

| NEUROBLASTOMA INTRAOPERATIVE PROBE COUNTS | | |
|---|---|---|
| Site | Counts/2 Sec. | Std. Deviation |
| Normal Tissue | | |
| Psoas Muscle | 33.3 | 0.9 |
| Diaphragm | 35.3 | 2.4 |
| Liver | 84.3 | 4.8 |
| Aorta | 62.7 | 5.4 |
| Gall Bladder | 225 | 3.7 |
| Tumor | | |
| Left Upper Quadrant Tumor | 116.3 | 4.9 |
| Left Upper Quadrant Tumor* | 86 | 11.5 |

TABLE 7

| | MEAN GAMMA PROBE COUNTS/2 SEC IN ABDOMINAL VISCERA TIME IN MINUTES | | | | | | |
|---|---|---|---|---|---|---|---|
| Abdominal Viscera | 15 | 30 | 60 | 165 | 230 | 320 | 450 |
| Liver | 200.0(15.9)* | 188.0(2.8) | 172.5(9.2) | — | 164.0(25.5) | 67.0(11.3) | 64.5(7.0) |
| Left Lobe | — | — | — | 96.5(3.5) | — | — | — |
| Right Lobe | — | — | — | 110.5(9.2) | — | — | — |
| Gall Bladder | 183.0(5.7) | 199.0(19.8) | 394.5(71.4) | — | 1650.0(5.7) | 1316.0(136.5) | 1178.5(161.9) |
| Pancreas | 68.5(12.0) | 82.0(4.2) | 105.0(0) | — | — | — | — |
| Duodenum | 84.5(91.2) | 68.5(6.4) | 140.0(4.2) | — | — | — | 60.0(4.2) |
| Porta Hepatis | 184.5(9.2) | — | — | — | — | — | — |
| Spleen | 100.5(16.3) | 84.0(1.4) | 70.5(2.1) | — | — | — | — |
| Right Kidney | 54.5(7.8) | 84.0(2.8) | 108.5(21.9) | — | — | — | 64.0(9.9) |
| Inferior Vena Cava | 103.5(7.8) | — | — | — | — | — | 47.5(3.5) |
| Aortic Bifurcation | 76.5(7.8) | 78.0(4.2) | 77.5(6.4) | 69.5(9.2) | 41.0(2.8) | 60.0(2.8) | 48.5(0.7) |

TABLE 8

| INTRAOPERATIVE OCCULT TUMOR LOCALIZATION UTILIZING $^{125}$I-TYR$^3$-OCTREOTIDE | | |
|---|---|---|
| | Gamma Probe Counts/2 sec. | |
| | Background | Occult Tumor |
| Tumor Extending to Diaphragm | 35.3(2.9) | 63.3(3.5) |
| Tumor Splenic Vein, Pancreas | 102.0(8.5) | 142.0(8.2) |

TABLE 9-continued

| NEUROBLASTOMA INTRAOPERATIVE PROBE COUNTS | | |
|---|---|---|
| Site | Counts/2 Sec. | Std. Deviation |
| Left Upper Quadrant Tumor* | 49 | 1.6 |
| Splenic Vein Involvement | 142 | 6.7 |
| Supra Celiac Region Residual Tumor | 63.3 | 2.8 |

*Different areas of tumor.

EXAMPLE 8

Figure 8:
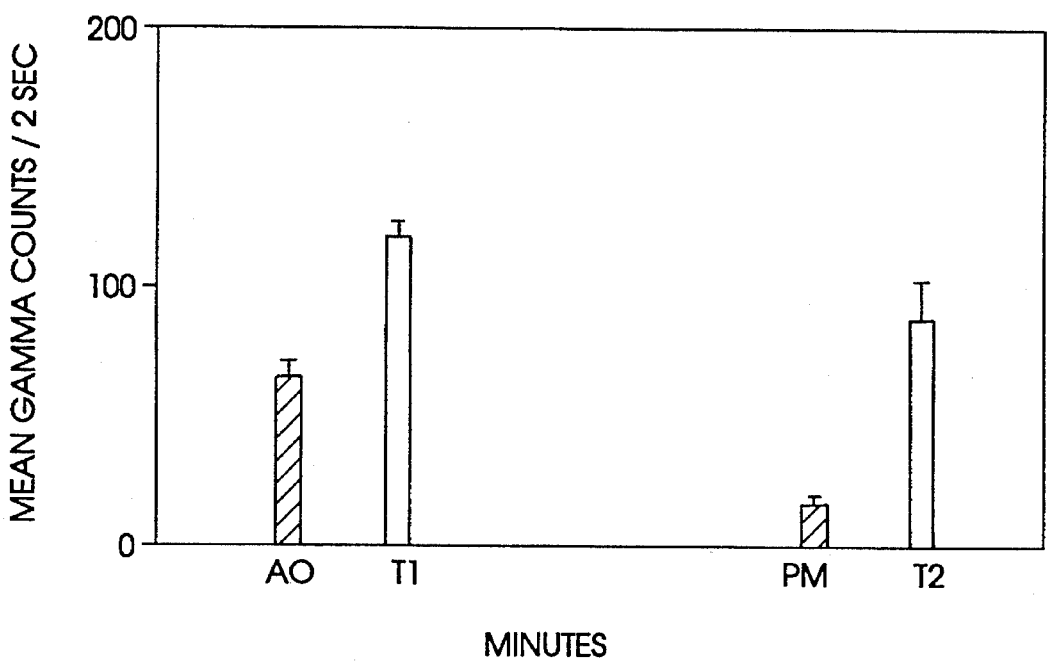

The patient (KG) was a 2-year-old white female who presented with fever, weight loss, and an abdominal mass. Computerized tomography and $^{123}$I-Tyr$^3$-octreotide scan both continued neuroblastoma. Challenge with unlabeled octreotide was not an available diagnostic or treatment modality at that time. The patient was administered 67 µCi of $^{125I}$Tyr$^3$-octreotide 20 hours prior to surgery. At the time of surgery, tumor was evident at the renal vein and upper left corner into the diaphragm. At 20 hours post injection, abdominal aorta counts were 63 while adjacent tumor had 120 counts/2 sec. Similarly, counts of about 33.3 were taken at the psoas muscle compared to 79 counts/2 sec. in adjacent tumor. These counts are depicted graphically in FIG. 8. Additionally, an occult tumor focus, having a count of 80 versus background of 62, was identified. Samples determined by the probe all were confirmed by pathology to be neuroblastoma. Thus, the ability of radiolabeled octreotide to identify neuroblastoma intraoperatively, even as long as 20–24 hours post-injection, is demonstrated.

EXAMPLE 9

The patient (DR) was a 36-year-old white female with a history of Zollinger-Ellison syndrome and recurrent peptic ulcer disease. She had first developed bleeding ulcers at approximately age eleven. A vagotomy and pyloroplasty had been performed six years prior to presentation but had resulted in no significant improvement of her condition. Although she was found to have elevated levels of gastrin, no tumor could be localized by conventional methods. An anglogram had revealed two hypervascular areas, one in the gallbladder fossa and a second in the head of the pancreas.

The patient's baseline gastrin level was 4,360 pg/mL. A somatostatin challenge test was performed as in previous Examples. Gastrin levels one and two hours post subcutaneous administration of 100 mcg of octreotide were 2,020 (53.6% reduction) and 1,614 pg/mL (63% reduction), respectively, predicting the presence of somatostatin receptors on the cells responsible for the increased gastrin production.

The patient underwent an exploratory laparatomy, wherein a gross visual and manual inspection provided no indication of a tumor. Intraoperative ultrasound of the pancreas, second portion of the duodenum, and the gallbladder fossa was unremarkable for focal masses. On intraoperative esophagogastroduodenoscopy, there was no lesion intraluminally in the stomach, duodenum, or second or third portions of the duodenum.

Figure 9:
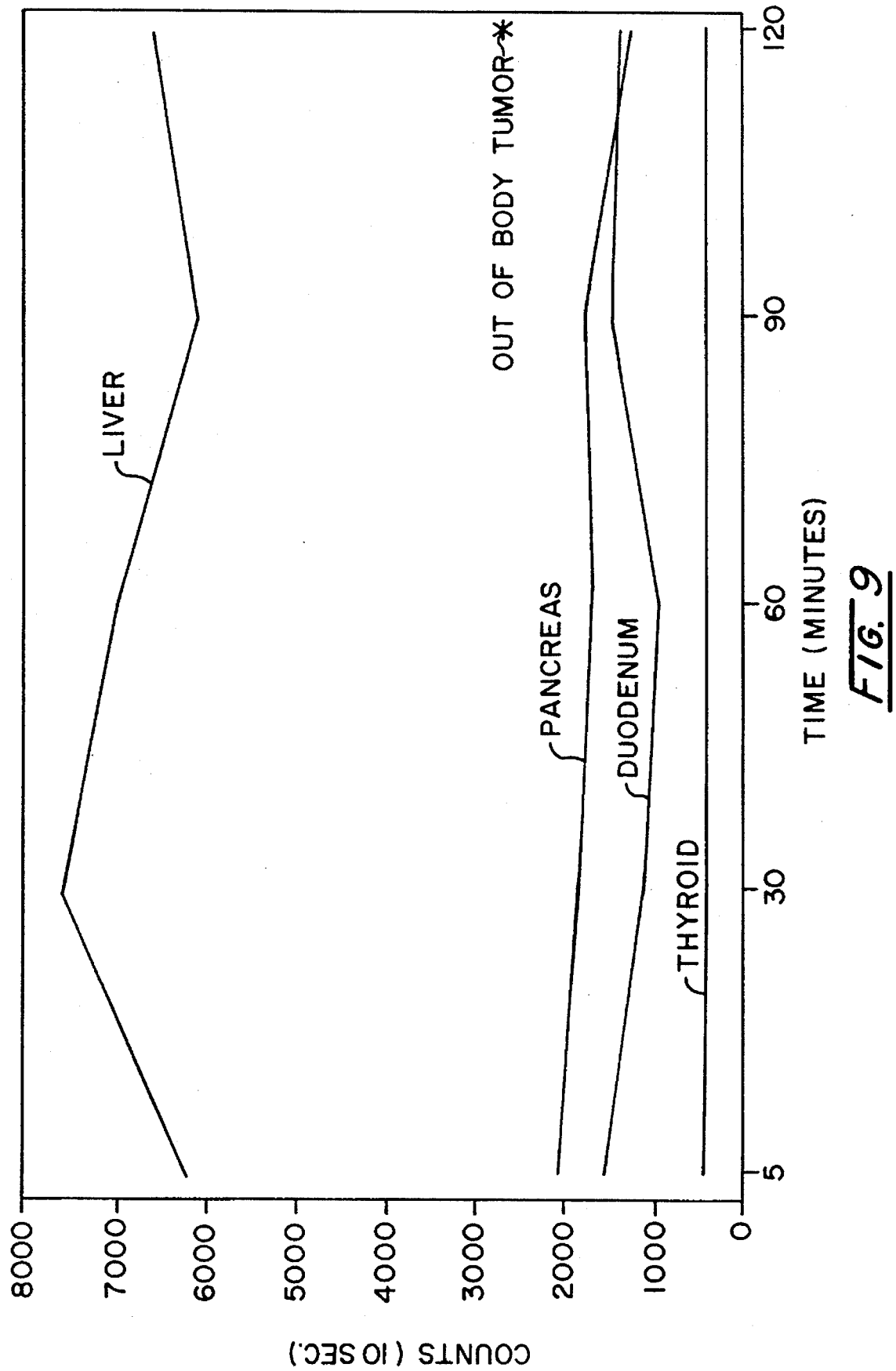

Following temporary occlusion of the common duct, the patient was injected with 98 mCi of the $^{125}$I-lanreotide radiolabeled and purified as discussed supra, and a Neoprobe® RIGS® model 1000 portable radiation detector was utilized to isolate the suspected occult gastrinoma. Measurements were taken of the thyroid, precordium, stomach, liver, duodenum, pancreas, first, second and distal portions of the small bowel, colon, bladder, and right and left kidneys. These measurements, shown in Table 9, were taken at half-hour intervals and are displayed graphically in FIG. 9. With the transducer placed in scan mode, the entire pancreas was scanned. Care was taken to avoid the liver as this would concentrate the radiolabel. A single source of increased counts was discovered, at the level of the portal lymph node, which was dissected out from beneath the common bile duct and the portal vein. This lymph node continued to register an increased signal following its removal from the field; however, pathology revealed a normal lymph node on frozen section. No other identifiable and consistent hot spots could be identified throughout the course of the scanning. A lateral duodenotomy was then performed to check for any missed intraluminal lesions; none was found. Unexpectedly, the patient's gastrin output normalized postoperatively, despite the fact that histologic examination of the portal lymph node had failed to demonstrate any tumor cells.

TABLE 10

| | GAMMA PROBE COUNT/2 SEC. TIME IN MINUTES | | | | | |
|---|---|---|---|---|---|---|
| Site | 2 | 5 | 30 | 60 | 90 | 120 |
| Pancreas | 2234 | 2061 | 1842 | 1691 | 1770 | 1214 |
| Stomach | 1349 | 2225 | 3129 | 2427 | 1855 | 2522 |
| Duodenum | 1552 | 1542 | 1107 | 957 | 1501 | 1333 |
| Proximal Small Bowel | 1565 | 2150 | 1493 | 1275 | 1555 | 1386 |
| Mid Small Bowel | 591 | 1435 | 1706 | 601 | 499 | 563 |
| Distal Small Bowel | — | 571 | 889 | 667 | 662 | 414 |
| Colon | 760 | 399 | 447 | 786 | 1153 | 503 |
| Bladder | 406 | 285 | 509 | 297 | 319 | 326 |
| Liver | 5306 | 6205 | 7605 | 6987 | 6072 | 6558 |
| Right Kidney | 1556 | 1140 | 950 | 978 | 521 | 1660 |
| Left Kidney | 1578 | 1321 | 1250 | 988 | 1282 | 580 |
| Thyroid | 570 | 477 | 404 | 389 | 424 | 386 |
| Heart | 762 | 488 | — | 462 | 502 | 423 |
| Precordium | — | 592 | 398 | 491 | 328 | 391 |
| Aorta | — | 853 | 1038 | 947 | 804 | 679 |

EXAMPLE 10

The patient (DA) was a 36-year-old white male with a long and complicated history of Type I multiple endocrine neoplasia (MEN). At the age of 16, he had experienced signs of syncope and was found to have multiple insulinomas, for which he underwent an 85% pancreatectomy. At the age of 29, he had presented with nephrolithiasis and had undergone a 3½-gland parathyroidectomy following a diagnosis of hyperparathyroidism. This initiated a search for other adenomas, and he was found to have a prolactin-secreting pituitary adenoma which was resected.

At the age of 30, he had presented for severe symptoms of epigastric pain and diarrhea. The workup at that time had demonstrated elevated gastric acid output and serum gastrin levels, and abdominal computerized tomography had revealed a 3–4 cm mass in the head of the remaining pancreatic tissue. This mass was enucleated, with monitoring of acid secretion and plasma gastrin levels throughout the procedure. Following tumor excision the acid secretion was decreased dramatically and the gastrin level was approximately halved. Various factors had complicated the patient's postoperative recovery, including a rapid rebound of acid secretion, controllable only with high doses of $H_2$ (histamine) blockers. Postop serum gastrin levels were consistently above 500 pg/ml. Immunocytochemical studies of the tumor revealed it to be predominantly glucagon-secreting rather than gastrin-secreting.

Approximately one year prior to his latest presentation, the patient had undergone transplantation of his remaining parathyroid tissue to his left forearm. He now presented for recurrence of elevated gastrin levels and intractable peptic disease. Upon exploratory laparatomy, the liver and stomach appeared normal. The duodenum was moderately thickened in the bulb. The common duct was mildly dilated approximately 1.1 cm in diameter. A very discrete mass 3.5 cm in diameter was identified in the paraduodenal area just lateral to the head of the pancreas. The patient also had a submucosal mass in the duodenal wall on the anterior surface of the second portion of the duodenum, measuring 7 mm in diameter, which was palpable. There was also some adenopathy in the retrogastric nodes in the vicinity of the celiac axis. These masses were not identified with intraoperative ultrasound, and no masses suggestive of tumor were noted in the head of the pancreas. Transduodenal illumination by endoscopy revealed the palpable nodule on the anterior portion of the second portion of the duodenum, but no other tumor in the duodenum.

Figure 10:
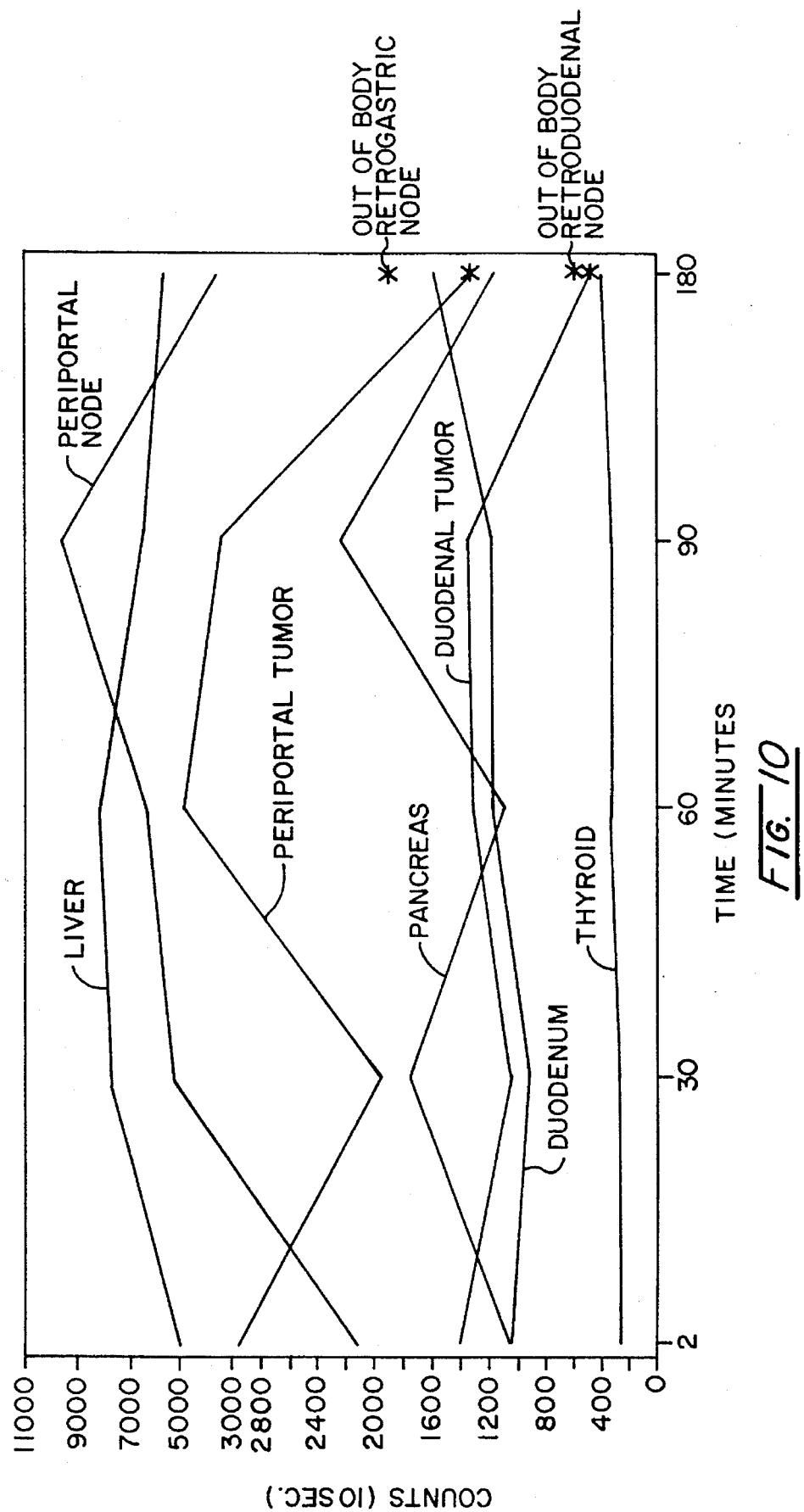

Radiolabeled lanreotide was prepared as described supra, and 149 mCi of $^{125}$I-lanreotide was injected, following temporary occlusion of the common duct. The Neoprobe® RIGS® model 1000 portable radiation detector was utilized intraoperatively to detect tumor binding of the radiolabeled somatostatin analog. Background counts over the thyroid, pancreas, stomach, small bowel, and colon were obtained, as shown in Table 10 and depicted graphically in FIG. 10. Tissues exhibiting elevated counts (background plus three standard deviations) were considered abnormal and excised. The counts were quite high in the suspicious nodules in the duodenal wall, the paraduodenal mass, and a palpable node in the retroduodenal area. However, the Neoprobe® radiation detector also detected two additional areas of increased activity and lymphadenopathy in the retrogastric area and one such area in the porta hepatis node. Thus, five separate "tumors" are depicted in FIG. 10, although histologic examination revealed visible tumor in the duodenal mass and in one retroduodenal node only. Postoperatively, the patient was biochemically cured, as evidenced by a gastrin level of 63 pg/ml. Thus, the ability of radiolabeled somatostatin congeners to identify gastrinomas and their metastases intraoperatively has been conclusively demonstrated.

TABLE 11

| Site | GAMMA COUNTS/2 SEC. TIME IN MINUTES | | | | | | |
|---|---|---|---|---|---|---|---|
| | 2 | 13 | 30 | 69 | 90 | 180 | Out-of-Body |
| Pancreas | 1056 | 1262 | 1749 | 1082 | 2241 | 1157 | |
| Stomach | 1221 | 1539 | 1177 | 2030 | 1937 | 1265 | |
| Duodenum | 1042 | 1325 | 922 | 1163 | 1185 | 1573 | |
| Proximal Small Bowel | 930 | 1540 | 1502 | 1076 | 1452 | 1133 | |
| Mid Small Bowel | 668 | 864 | 787 | 1027 | 537 | 664 | |
| Distal Small Bowel | 436 | 593 | 559 | 979 | 754 | 516 | |
| Colon | 663 | 931 | 425 | 646 | 436 | 503 | |
| Bladder | 316 | 304 | 244 | 269 | 667 | 305 | |
| Liver | 7946 | 7085 | 7748 | 8109 | 6458 | 5554 | |
| Right Kidney | 828 | 1346 | 1203 | 1448 | 1266 | 1668 | |
| Left Kidney | 999 | 989 | 874 | 887 | 978 | 1018 | |
| Thyroid | 253 | 251 | 268 | 325 | 327 | 387 | |
| Heart | 478 | 501 | 616 | 539 | 547 | 427 | |
| Periportal Node | 2159 | 6249 | 5299 | 6294 | 9599 | — | 3623 |
| Duodenal Tumor | 1415 | 2080 | 1052 | 1307 | 1344 | — | 477 |
| Periportal Tumor | 2944 | 2677 | 1956 | 3336 | 3081 | — | 1315 |
| Retroduodenal Node | — | — | — | — | — | — | 573 |
| Retrogastric Node | — | — | — | — | — | — | 1890 |

We claim:

1. A method for the detection and differentiation of neoplastic tissue in a patient suspected of having neoplastic tissue associative with a somatostatin congener and which neoplastic tissue may be occult, which comprises the steps of:

(a) administering a biochemical marker-inhibiting dose of unlabeled somatostatin congener to a patient;

(b) monitoring a biochemical marker associated with said neoplastic tissue to determine whether the administered somatostatin congener reduced the presence of said marker in said patient;

(c) if the monitored presence of said marker in said patient was reduced, then administering radiolabeled somatostatin congener to said patient;

(d) accessing said patient with a radiation detection probe for detecting and differentiating tissue exhibiting elevated levels of radiation; and (e) extirpating tissue detected and differentiated in step (d).

2. The method of claim 1, wherein said congener is an octapeptide.

3. The method of claim 2, wherein said congener is one or more of lanreotide or Tyr$^3$-octreotide.

4. The method of claim 1, wherein said neoplastic tissue comprises a neuroendocrine tumor.

5. The method of claim 1, wherein said patient is surgically accessed and a manually-positionable portable radiation detection probe is used in vivo to determine said elevated levels of radiation.

6. The method of claim 1, wherein said patient is accessed with an endoscope or laparoscope and a remotely-positionable radiation detector is used in vivo to determine said elevated levels of radiation.

7. The method of claim 1, wherein said radiolabel comprises $^{125}$I.

8. The method of claim 1, wherein said biochemical marker monitored is one or more of growth hormone, adrenocorticotropin hormone, prolactin, thyroid stimulating hormone, insulin, glucagon, motilin, gastric inhibitory peptide (GIP), vasoactive intestinal peptide (VIP), secretin, cholecystokinin, bombesin, or gastrin-releasing peptide (GRP).

9. The method of claim 1, wherein said unlabeled somatostatin congener in step (a) is administered in a dose ranging from between about 100 and 3,000 μg.

10. The method of claim 1, wherein said radiolabeled somatostatin congener administered in step (c) is delivered to the neoplastic tissue in a dose ranging from about 0.1 to 1 mCi.

11. The method of claim 10, wherein said radiolabel comprises $^{125}$I.

12. The method of claim 1, wherein said radiolabeled somatostatin congener administered in step (c) is delivered to the neoplastic tissue in a dose ranging from about 0.1 ng to 10 μg.

13. The method of claim 10, wherein said radiolabeled somatostatin congener administered in step (c) is delivered to the neoplastic tissue in a dose ranging from about 0.1 ng to 10 μg.

14. The method of claim 11, wherein said radiolabeled somatostatin congener administered in step (c) is delivered to the neoplastic tissue in a dose ranging from about 0.5 ng to 1 μg.

15. A method for the detection and differentiation of neoplastic tissue in a patient suspected of having neoplastic tissue associative with a somatostatin congener and which neoplastic tissue may be occult, which comprises the steps of:

(a) administering a biochemical marker-inhibiting dose of unlabelled octapeptide somatostatin congener to a patient;

(b) monitoring a biochemical marker associated with said neoplastic tissue to determine whether the administered somatostatin congener reduced the presence of said marker in said patient;

(c) if the monitored presence of said marker in said patient was reduced, then administering to said patient one or more of lanreotide and $^{125}$I-Tyr$^3$-octreotide;

(d) accessing said patient with a radiation detection probe for detecting and differentiating tissue exhibiting elevated levels of radiation; and (e) extirpating tissue detected and differentiated in step (d).

16. The method of claim 15, wherein said neoplastic tissue comprises a neuroendocrine tumor.

17. The method of claim 15, wherein said patient is surgically accessed and a manually-positionable portable radiation detection probe is used in vivo to determine said elevated levels of radiation.

18. The method of claim 15, wherein said patient is accessed with an endoscope or laparoscope and a remotely-positionable radiation detector is used in vivo to determine said elevated levels of radiation.

19. The method of claim 15, wherein said unlabeled somatostatin congener in step (a) is administered in a dose ranging from between about 100 and 3,000 μg.

20. The method of claim 19, wherein said radiolabeled somatostatin congener administered in step (c) is delivered to the neoplastic tissue in a dose ranging from about 0.1 to 1 mCi.

21. The method of claim 20, wherein said radiolabeled somatostatin congener administered in step (c) is delivered to the neoplastic tissue in a dose ranging from about 0.1 to 10 μg.

22. A method for the detection and differentiation of neoplastic tissue in a patient suspected of having neoplastic tissue associative with a somatostatin congener and which neoplastic tissue may be occult, which comprises the steps of:
(a) administering to a patient a biochemical marker-inhibiting dose of a first somatostatin congener radiolabeled with an isotope capable of being externally scanned;
(b) externally scanning said patient to determine the presence of neoplastic tissue by the uptake of said first radiolabeled somatostatin congener;
(c) if said neoplastic tissue is determined in step (b), then administering a second radiolabeled somatostatin congener to said patient;
(d) accessing said patient with a radiation detection probe for detecting and differentiating with said probe tissue exhibiting elevated levels of radiation; and
(e) extirpating tissue detected and differentiated in step (d).

23. The method of claim 22, wherein said congener is an octapeptide.

24. The method of claim 23, wherein said congener is one or more of lanreotide or Tyr$^3$-octreotide.

25. The method of claim 24, wherein said first radiolabel in step (a) is $^{123}$I.

26. The method of claim 25, wherein said second radiolabel in step (c) is $^{125}$I.

27. A method for the detection and differentiation of neoplastic tissue in a patient suspected of having neoplastic tissue associative with a somatostatin congener and which neoplastic tissue may be occult, which comprises the steps of:
(a) administering a radiolabeled somatostatin congener to said patient;
(b) accessing said patient with a radiation detection probe for detecting and differentiating with said probe tissue exhibiting elevated levels of radiation; and
(e) extirpating tissue detected and differentiated in step (b).

28. The method of claim 27, wherein said congener is an octapeptide.

29. The method of claim 28, wherein said congener is one or more of lantrestide or Tyr$^3$-octreotide.

30. The method of claim 29, wherein said radiolabel in step (b) is $^{125}$I.

31. The method of claim 29, wherein said patient is surgically accessed and a manually-positionable portable radiation detection probe is used to determine said elevated levels of radiation.

32. The method of claim 29, wherein said patient is accessed with an endoscope or laparoscope and a remotely-positionable radiation detector is used in vivo to determine said elevated levels or radiation.

33. The method of claim 29, wherein said radiolabeled somatostatin congener administered in step (b) is delivered to the neoplastic tissue in a dose ranging from about 0.1 to 1 mCi and said radiolabeled somatostatin congener administered in step (b) is delivered to the neoplastic tissue in a dose ranging from about 0.1 to 1 µg.

* * * * *